US012806062B2

(12) United States Patent
Stroebech et al.

(10) Patent No.: US 12,806,062 B2
(45) Date of Patent: Nov. 24, 2026

(54) OSTOMY BASE PLATE AND METHODS OF PREVENTING CONTAMINATION OF THE ADHESIVE OF THE BASE PLATE

(71) Applicant: Coloplast A/S, Humlebaek (DK)

(72) Inventors: Esben Stroebech, Hoersholm (DK); Michael Hansen, Gilleleje (DK); Alexandra Liv Vest Loevdal, Charlottenlund (DK); Niels Peter Emme, Hellerup (DK)

(73) Assignee: Coloplast A/S, Humlebaek (DK)

( * ) Notice: Subject to any disclaimer, the term of this patent is extended or adjusted under 35 U.S.C. 154(b) by 543 days.

(21) Appl. No.: 18/023,007

(22) PCT Filed: Aug. 23, 2021

(86) PCT No.: PCT/DK2021/050261
§ 371 (c)(1),
(2) Date: Feb. 24, 2023

(87) PCT Pub. No.: WO2022/042810
PCT Pub. Date: Mar. 3, 2022

(65) Prior Publication Data

US 2023/0301817 A1 Sep. 28, 2023

(30) Foreign Application Priority Data

Aug. 27, 2020 (DK) ........................... PA 2020 70555

(51) Int. Cl.
*A61F 5/443* (2006.01)
*A61F 5/44* (2006.01)
*A61F 5/449* (2006.01)

(52) U.S. Cl.
CPC ............ *A61F 5/443* (2013.01); *A61F 5/4401* (2013.01); *A61F 5/449* (2013.01)

(58) Field of Classification Search
CPC .......... A61F 5/443; A61F 5/445; A61F 5/449; A61F 5/4401; A61F 5/4404
See application file for complete search history.

(56) References Cited

U.S. PATENT DOCUMENTS 5,384,174 A 1/1995 Ward et al.
5,496,296 A 3/1996 Holmberg
(Continued)

FOREIGN PATENT DOCUMENTS

WO 2000044324 A1 8/2000
WO 2007140785 A1 12/2007
(Continued)

*Primary Examiner* — Andrew J Mensh
*Assistant Examiner* — Hans Kaliher
(74) *Attorney, Agent, or Firm* — Coloplast Corp., Coloplast A/S; Nick Baumann

(57) ABSTRACT

Abase plate for an ostomy appliance including a removable protection element provided on a proximal adhesive surface of the base plate wherein an uptake portion is provided on the removable protection element and is adapted to take up stomal effluents. Further disclosed are methods of preventing stomal effluents from the stoma from contaminating the adhesive material of the base plate during application of the base plate to the skin surface around the stoma of the user, as well as a kit of parts and an accessory for a base plate of an ostomy appliance.

21 Claims, 15 Drawing Sheets

(56) References Cited

U.S. PATENT DOCUMENTS

| | | | | |
|---|---|---|---|---|
| 5,998,694 | A * | 12/1999 | Jensen | A61F 13/023 602/56 |
| 6,530,910 | B1 | 3/2003 | Pomplun et al. | |
| 8,071,126 | B2 * | 12/2011 | Sekiguchi | A61L 15/44 602/57 |
| 2007/0005032 | A1 | 1/2007 | Shan et al. | |
| 2009/0312685 | A1 * | 12/2009 | Olsen | A61F 5/443 604/386 |
| 2011/0213322 | A1 | 9/2011 | Cramer et al. | |
| 2011/0245789 | A1 | 10/2011 | Buus | |
| 2013/0090617 | A1 | 4/2013 | Uvebom | |
| 2014/0303594 | A1 * | 10/2014 | Stockholm | A61K 9/703 156/60 |
| 2015/0073325 | A1 * | 3/2015 | Oeelund | A61L 15/225 602/46 |
| 2018/0250156 | A1 | 9/2018 | Lam | |
| 2018/0263804 | A1 | 9/2018 | Stroebech et al. | |
| 2018/0311066 | A1 | 11/2018 | Hansen et al. | |
| 2019/0070034 | A1 * | 3/2019 | Udayakumar | A61L 24/043 |
| 2020/0022879 | A1 * | 1/2020 | McMichael | A61F 13/36 |
| 2020/0030134 | A1 | 1/2020 | Hopper | |
| 2020/0163792 | A1 | 5/2020 | Schertiger | |

FOREIGN PATENT DOCUMENTS

| | | | |
|---|---|---|---|
| WO | 2011091801 | A1 | 8/2011 |
| WO | 2013156034 | A1 | 10/2013 |
| WO | 2017152921 | A1 | 9/2017 |
| WO | 2018054442 | A1 | 3/2018 |
| WO | 2018188708 | A1 | 10/2018 |

* cited by examiner

OSTOMY BASE PLATE AND METHODS OF PREVENTING CONTAMINATION OF THE ADHESIVE OF THE BASE PLATE

BACKGROUND

Stomal output often contains body fluids and visceral contents that are aggressive to both the skin of a user and to ostomy appliances, in particular these have a detrimental effect on the efficiency and integrity of the adhesive materials that are applied to attach the ostomy appliance to the user's skin surface. Some ostomists may choose or must wear their appliance for prolonged periods of time. For users in general, and particularly for this group of ostomists safe, reliable, and efficient ostomy appliances are highly desirable. Numerous attempts have been made to provide ostomy appliances to meet demands, such as prolonged wear time, but the provision of sufficient efficiency to achieve a satisfactory long wear time of ostomy appliances has historically been an unmet need.

Ostomists and health care professionals alike would welcome improvements in ostomy appliances to better meet such demands.

SUMMARY

The present disclosure provides aspects of a base plate of an ostomy appliance including an uptake portion provided on a removable protection element provided on at least a proximal surface of the adhesive of the base plate. The uptake portion for the base plate of the ostomy appliance is adapted to help a user to prevent unintended and detrimental contamination of the adhesive material of the base plate with stomal effluents from the stoma during application of the ostomy appliance to the peristomal skin surface around the stoma of the user. An accessory including an uptake portion and a kit of parts including an accessory according to the disclosure is also disclosed. A method of preventing contamination of an adhesive material of a base plate for an ostomy appliance during application of the base plate to the peristomal skin surface around a user' stoma is also disclosed. Further, a method for training a user of an ostomy appliance to prevent contamination of an adhesive material of a base plate of the ostomy appliance during application of the base plate to the peristomal skin surface around a user's stoma is also disclosed. Inventive aspects and embodiments of the disclosure are defined in the appended claims.

BRIEF DESCRIPTION OF THE DRAWINGS

The accompanying drawings are included to provide a further understanding of embodiments and are incorporated in and constitute a part of this specification. The figures illustrate embodiments and together with the description serve to explain principles of embodiments. Other embodiments and many of the intended advantages of embodiments will be readily appreciated as they become better understood by reference to the following detailed description.

Various exemplary embodiments and details are described hereinafter, with reference to the figures when relevant. It should be noted that the figures may or may not be drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and may be practiced in any other embodiments even if not so illustrated, or if not so explicitly described.

FIG. 7 is a schematic, perspective view of one embodiment of a base plate as disclosed herein.

Figure 1:
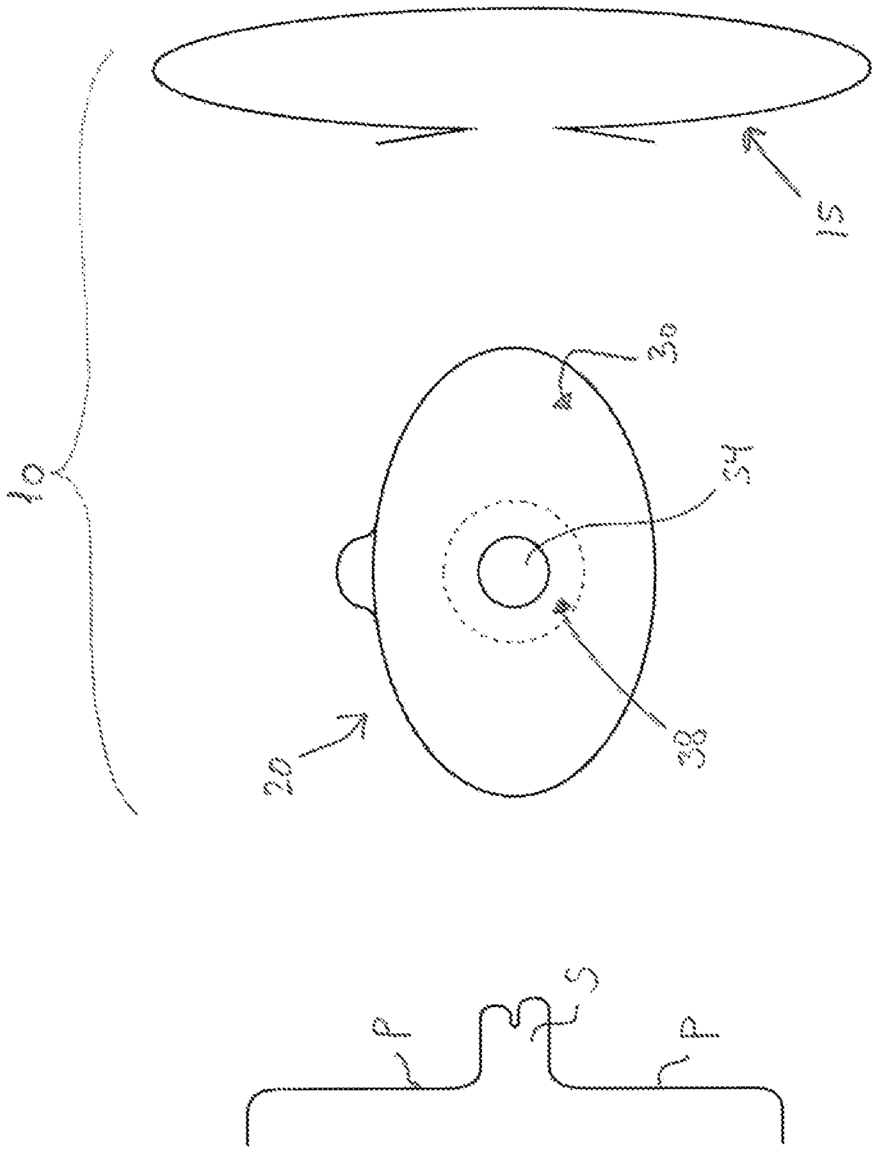
FIG. 1 is a schematic view of one embodiment of a base plate for an ostomy appliance.

Each of FIGS. 11-16 is a plan view of one embodiment of a base plate according to the invention.

DETAILED DESCRIPTION

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized, and structural or logical changes may be made without departing from the scope of the present invention. The following detailed description, therefore, is not to be taken in a limiting sense.

It is to be understood that the features of the various embodiments described herein may be combined with each other, unless specifically noted otherwise.

Throughout this disclosure, the words "stoma" and "ostomy" are used to denote a surgically created opening bypassing the intestines or urinary tract system of a person. The words may be used interchangeably, and no differentiated meaning is intended. The same applies for any words or phrases derived from these, e.g. "stomal", "ostomies" etc. Also, the solid and liquid wastes emanating from the stoma may be referred to as both stomal “effluents”, “output,” “waste(s),” “fluids” and other interchangeably. A person or subject having undergone ostomy surgery may be referred to as “ostomist” or “ostomate”—moreover, also as “patient” or “user”. However, the phrase “user” can also relate or refer to a health care professional (HCP), such as a surgeon or an ostomy care nurse or others. Addressing ‘stoma’ herein refers at least to ostomy, ileostomy and urostomy as the problem of contamination of the adhesive surface of a base plate can be caused by stomal effluents in any of these conditions.

In the following, whenever referring to proximal side or surface of a device or part of an appliance (or component), the referral is to the skin-facing side or surface, when the ostomy appliance is worn by a user. Likewise, whenever referring to the distal side or surface of an appliance or part of an appliance, the referral is to the side or surface facing away from the skin, when the ostomy appliance is worn by a user. In other words, the proximal side or surface is the side or surface of something being closest to the user, when the appliance is fitted on a user and the distal side or surface is the opposite side surface—the side or surface of something farthest away from the user in use.

The “axial” direction is defined as the direction of the stoma when the appliance is worn by a user. Thus, the axial direction is generally perpendicular to the stomach skin or abdominal skin surface of the user.

The radial direction is defined as transverse to the axial direction that is transversely to the direction of the stoma. In some sentences, the words “inner” and “outer” may be used. These qualifiers should generally be perceived with reference to the radial direction, such that a reference to an “outer” element means that the element is farther away from a centre portion of a thing, e.g. a base plate for an ostomy appliance than an element referenced as “inner”. In addition, “innermost” should be interpreted as the portion of a thing or component forming a centre of the component and/or being adjacent to the centre of the component or alternatively to an inner (e.g. peripheral) edge thereof. In analogy, “outermost” should be interpreted as a portion of a component forming an outer (e.g. peripheral) edge or outer contour of a component and/or being adjacent to that outer edge or outer contour.

In this specification, end means endmost and end portion means that segment that is adjacent to and extends from the end.

The use of phrases such as (but not limited to) “substantially” and “approximately” as qualifiers of certain features or effects in this disclosure, is intended to simply mean that any deviations are within tolerances that would normally be expected by the skilled person in the relevant field.

The phrase “adjacent”, such as in the wording “adjacent the peristomal skin surface” in claim 1 and other places, should be interpreted as being “close to and/or in contact with, or temporarily brought into contact with, but not attached to the peristomal skin surface.”

The wording “uptake” and “take up” in relation to a component or effect should be understood in its normal technical sense, i.e. as meaning something which is capable of incorporating and retain something else (another material or matter) in it, mainly by being brought into contact with that other material or matter.

During application of a base plate to the peristomal skin around a stoma, great care must be taken not to contaminate the adhesive material of the base plate with stomal effluents. However, avoiding contamination of the adhesive material of the base plate has proven very difficult for users. A stoma-receiving opening in the base plate is generally provided at manufacture or cut by the user to fit closely around the stoma thus leaving only little extra space around the stoma during application of the base plate. The risk of touching the stoma and/or stomal effluents exuded from the stoma with the edge of the stoma-receiving opening of the base plate or other portion of the adhesive material during application of a base plate is therefore significant. Even a small amount or droplet of stomal effluent on the adhesive material can quickly spread or disperse to contaminate a substantial area of the adhesive material, a problem often worsened as the base plate is subsequently subjected to finger pressure to adhere the adhesive material against the peristomal skin surrounding the stoma (the adhesive material is often of the pressure-sensitive kind). Moreover, all stomas have individual sizes and deviating shapes and contours, also adding to making the task of applying without touching and thus avoiding contamination of the adhesive surface of the base plate difficult to ensure. A still further problem is that it is often hard for a user to see what he or she is doing when applying a base plate to their belly because the stoma is often located on a lower (or downwardly facing) portion of the stomach skin, at least when the user is in a standing position.

When a base plate is prepared for application to the peristomal skin surface, the size of the stoma-receiving opening is chosen (standard sizes available from supplier) or adjusted (by user customization) to the contour, size and shape of the stoma. The user may for example be instructed to cut the opening in a shape such that the adhesive material of the base plate will only adhere to the peristomal skin (and not to the stoma itself) and to provide an approximately 1 mm boundary zone (gap) between the cut stoma-receiving opening and the mucous membrane of the stoma. Because the stoma-receiving opening is therefore often prepared to be only slightly larger than the stoma itself, contamination of the adhesive material on the proximal surface of the base plate before bonding to the skin surface is likely to unintentionally occur. Typically, a user is instructed to leave as little room between the stoma and the (customized) stoma-receiving opening to prevent stomal effluents from entering between the adhesive and the skin surface, to avoid damage to the peristomal skin from moisture (skin maceration) and/or aggressive constituents of the stomal effluents, e.g. incl. enzymes produced in the intestines. However, when following that instruction, it is often very difficult to avoid contact between the stoma and/or the peristomal skin surface and the edge of the stoma-receiving opening during application of the base plate.

Experience has shown that when stomal waste, i.e. urine and/or faeces and other constituents, comes into contact with the adhesive material of a base plate, the “adhesiveness” and/or tack of the adhesive material (or at least the surface thereof) can decrease temporarily or permanently, thereby promoting the creation of chambers or canals in the adhesive material for stomal effluents to pass through because the adhesive material slips from the peristomal skin surface due to the reduced tack and/or because the adhesive material deteriorates (which leads to further loss of tack etc.). Small amounts of effluents on the adhesive material may cause this reduction in tack to occur and pave the way for very premature failure of the adhesive material already during application of a fresh base plate, which at least eventually (and from experience very rapidly) results in leakage with soiling of the user’s clothes and a stigmatising experience for the user as a consequence. Avoiding contamination of the adhesive material during application of a base plate is therefore a key problem connected with the application of base plates for ostomy appliances, which the inventors behind the present disclosure therefore set out to solve.

The inventors have observed from tests and studies that contamination of the adhesive material happens rather frequently e.g. because the inner peripheral edge of the stoma-receiving opening of a base plate (which edge is a very short distance from the stoma surface) is highly prone to contact or touch and "scrape off" stomal effluents from the stoma surface when the user shifts or moves the base plate towards the peristomal skin surface for bonding thereto.

Importantly, it has further surprisingly been observed by the inventors that in many cases a practically invisible layer of mucin is present on the stoma, and/or at the root of the stoma and/or on the peristomal skin surface, even in cases where the stoma and peristomal skin surface has been thoroughly wiped off by the user and otherwise looks clean before initiating the process of applying the base plate to the peristomal skin surface. Apart from stomal wastes, "stomal effluents" can include mucus and mucins coming from the mucous membrane of the stoma and out of the stoma from the intestinal walls. Mucus is a slippery aqueous secretion produced by, and covering, mucous membranes. Mucins are a family of high molecular weight, heavily glycosylated proteins (glycoconjugates) produced by epithelial tissues in most animals, such as in the intestinal walls of humans. Studies indicate that upon wiping a stoma surface clean with tissue paper, a layer of a thickness of about 50-100μ of mucin develops on the stoma surface within 2 minutes from the wiping. In an attempt to make a scalable understanding of the phenomenon, the inventors have considered a theoretical stoma of 030 mm and with a "height" of 30 mm, and have calculated a theoretical production of mucin from the stoma between 5-30 mL per 24 hours.

Figure 8B:
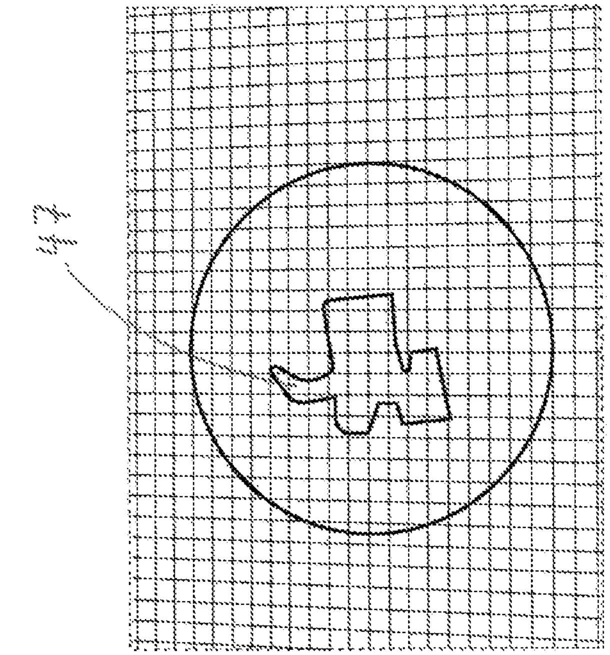
FIGS. 8A-8B illustrate the mechanism behind one of the problems that the invention aims to solve.
Figure 8A:
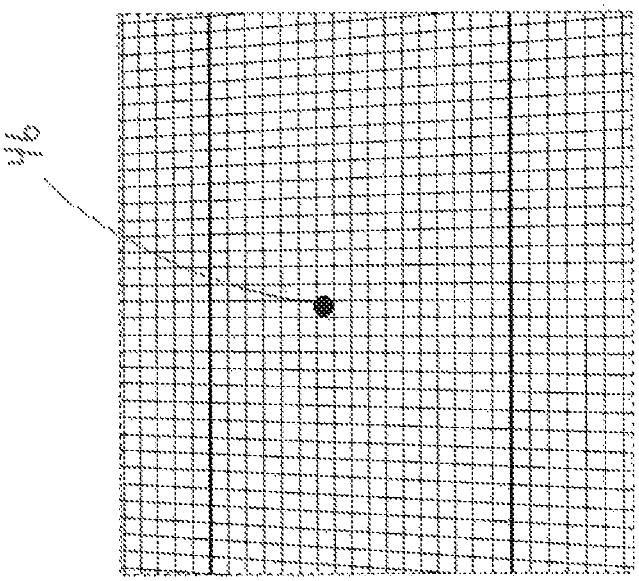

For additional understanding, the issue of contamination of the adhesive material is visualized in FIGS. 8A-8B, in which a droplet of coloured liquid (illustrating stomal effluent and coloured in order to enhance visibility) is placed on a glass plate (illustrating the skin). In FIG. 8B, a second glass plate (illustrating a base plate for an ostomy appliance) is placed over the droplet, and the droplet is thereby squeezed and spread out over a larger area. The contours of the spread-out droplet are drawn up to visualize the area now being contaminated with liquid. As can be seen, the droplet of liquid is now squeezed out to cover a substantial portion of the glass plate. It is believed that this same mechanism applies on the adhesive surface of a base plate having been subjected to a droplet or splash of stomal effluent on it when it is applied to the peristomal skin surface around a stoma.

It is found that when stomal effluents, and particularly mucin, come into contact with the adhesive material, the adhesive material rapidly (practically instantaneously) loses it adhesive capability and tack. This means that the adhesive cannot adhere to the peristomal skin surface in the areas contaminated by mucin. This then in turn means that "canals" or "paths" can be created between the (non-adhered) adhesive material and the peristomal skin surface in the contaminated areas, in which canals or paths urine and/or faeces released from the stoma can travel. This in turn provides the possibility for the urine and/or faeces to harm and/or degrade the adhesive material in or along the canals or paths, thereby leading to further undermining of adhesion and tack and thus to a vicious circle of adhesive breakdown causing premature leakage. In other words, the adhesive material is very likely to being degraded or "weakened" already from the initial attachment of a fresh base plate, because of the stomal effluents, and particularly the mucin, coming into contact with the adhesive material during application of the base plate. This is found to result in premature failure of the adhesive with ensuing leakage and reduction of the wear time of the base plate as consequences.

Another issue identified by the inventors is that users have difficulty in avoiding contact with the stoma's surface, not only during application, but also in many cases users provide so poor customization/adaptation of the stoma-receiving opening and/or positioning of the base plate around the stoma that the base plate will be in direct contact with the stoma surface throughout its lifetime (e.g. at the edge along the stoma-receiving opening). Being in constant contact with the base plate product has been found to cause the stoma to continuously release or secrete a significant and increased amount of mucus and mucin, because the stoma is irritated by the enduring contact and attempts to repel the base plate.

The present application discloses a base plate which provides a user with the possibility to remove stomal effluents including mucus, and particularly mucin, from the peristomal skin surface, prior to adhesion of a base plate to the peristomal skin surface and to avoid contamination of the adhesive material of the base plate and thus to get an optimal bonding by uncontaminated adhesive material of the base plate to the peristomal skin surface.

A base plate according to aspects of the disclosure facilitates secure attachment of the base plate of an ostomy appliance by decreasing or eliminating the risk of contamination of the adhesive material of the base plate during application thereof to the skin. This is achieved inter alia by eliminating the possibility of stomal effluents including mucin from contaminating the adhesive material of the base plate particularly by removing almost invisible seeped-out effluents from the peristomal skin surface before the adhesive of the base plate is brought into contact with the peristomal skin surface. In some embodiments, the base plate includes solutions to additionally mitigate the problem of contamination at an inner peripheral edge of the stoma-receiving opening.

Thus, in a first aspect, the present disclosure relates to a base plate for an ostomy appliance. The base plate comprises a carrier layer having a distal surface and a proximal surface. The base plate also comprises an adhesive material provided on the proximal surface of the carrier layer and adapted to adhere the base plate to a peristomal skin surface around a stoma of a user. Further, the base plate comprises a removable protection element provided on at least a proximal surface of the adhesive material. A stoma-receiving opening extends through the carrier layer, the adhesive material, and the removable protection element of the base plate. The carrier layer is suitably made from a polymer material such as polyolefin types e.g. polyethylene, polypropylene or polybutylene, polyamide, polyurethane, polyvinyl acetate and/or ethylene vinyl acetate. Other suitable polymer materials for the carrier layer can be acceptable. The adhesive material can suitably be a pressure-sensitive adhesive of one or more of the types generally applied in the field of ostomy appliances.

An uptake portion surrounding the stoma-receiving opening is provided on at least a proximal surface of the removable protection element and is configured to take up stomal effluents to prevent the adhesive material from being contaminated by stomal effluents. This is particularly useful as the ostomy appliance is guided to a desired position adjacent the peristomal skin surface with the user's stoma engaging the stoma-receiving opening. At least the uptake portion is adapted to be removed when the base plate is in a desired position around the stoma. Surrounding is intended to mean immediately around, with no distance (radial space) between the uptake portion and the stoma-receiving opening.

In embodiments, the uptake portion is releasably adhered to the proximal surface of the removable protection element. In embodiments, the uptake portion is provided on a liner or sheet material which in turn is releasably adhered to the removable protection element. In embodiments, the liner or sheet material is releasably adhered to the removable protection element by a double-sided adhesive tape, which can include an identical type of adhesive on both sides or include different adhesive types on each side. Suitable adhesives include, but are not limited to, acrylic adhesives, hotmelts typically based on ethylene-vinyl-acetates (EVAs), polyurethane-based adhesive provided as a film or net or spun or other adhesive structure. Additionally, curable adhesive systems are also an option.

In embodiments, the uptake portion is integral with and forms at least a portion of the proximal surface of the removable protection element. In non-limiting examples, being "integral with" is to be understood as being inbuilt or incorporated into another structure (the removable protection element) or to be inseparably connected to the other structure, such as, but not exclusively, by a permanent, strong adhesive. Alternatively, the uptake portion can be integral with the removable protection element by being welded or laminated or otherwise physically anchored or fixed to the proximal surface of the removable protection element. In other words, the components being integral with each other cannot be separated without one or both being destroyed and/or losing their functionality.

In embodiments, the stoma-receiving opening can be provided in a centre portion of the base plate. Alternatively, the stoma-receiving opening can be provided radially offset from a centre portion of the base plate.

In embodiments, the removable protection element and the uptake portion are adapted to be removed in one and the same removal action when the base plate is in a desired position around the stoma. It is to be understood that in those embodiments wherein the uptake portion is releasably adhered to the proximal surface of the removable protection element, the uptake portion is independently removable, such as by a first removal action and the removable protection element is separately and independently removable, such as by a second removal action. Correspondingly, in embodiments wherein the uptake portion is integral with and forms at least a portion of the proximal surface of the removable protection element, the uptake portion and the removable protection element are configured to be removed together in one and the same removal action.

In some implementations, reflecting the user's individual stoma profile, the engagement between the stoma-receiving opening and the user's stoma includes allowing the user's stoma to extend at least partway through the opening (typical case of a protruding or even a prolapsing stoma). In other implementations, the engagement between the stoma-receiving opening and the user's stoma requires only that the stoma-receiving opening surrounds the stoma, e.g. that the opening is provided substantially around and at level with the stoma's 'mouth' ('stoma' means 'mouth' in Greek) at the peristomal skin surface (typical cases of retracted, flush or low profile stomas). Use of the term 'engaging' or 'engagement' is intended to encompass all these various stoma profiles.

In accordance with the invention, the uptake portion is configured to take up stomal effluents that it engages (or vice versa, stomal effluents that engages the uptake portion). Thus, in situations where stomal effluents (particularly mucins) seep onto the surface of the stoma and/or have contaminated and/or wetted the peristomal skin surface around the stoma, the stomal effluents are taken up by the uptake portion. In some cases, the mucin can manifest as only a thin and almost invisible (unnoticeable) layer on the skin surface, and even very small amounts of mucin are found to be sufficient to compromise the correct functioning of the adhesive material of the base plate.

The taken-up stomal effluents are removed with and when the uptake portion, or both the uptake portion and the removable protection element of the base plate, is/are removed by the user. The removal of taken-up effluents means that the adhesive material and the peristomal skin surface is uncontaminated before adhering the base plate to the peristomal skin surface. This greatly reduces or even eliminates the risk of compromising the adhesive material e.g. when replacing a base plate for a used one and consequently greatly improves the chances for the user to put on a base plate with a perfectly uncompromised adhesive material, which in turn reduces the risk of adhesive failure, leakage and other detrimental effects as discussed above. When the adhesive material of a fresh base plate is not compromised from "the beginning", and the peristomal skin surface is free from effluents, an increase in the overall wear time of the base plate (and in turn the entire ostomy appliance) is achieved resulting in both better user health (e.g. better skin condition/less inconvenience) and lower costs (e.g. the user him/herself and the health authorities must fund a lower overall number of ostomy appliances). It is to be understood that the uptake portion is not only able to take up the stomal effluents from the peristomal skin surface, but also to effectively retain the taken-up effluents, at least for a period of time suitable to allow the user to finalize the base plate application process, including safe disposal of waste.

According to the disclosure, the uptake portion is configured to take up stomal effluents and prevent contamination of the adhesive material. This is particularly useful as the base plate is guided to a desired position on or adjacent the peristomal skin surface with the user's stoma engaging the stoma-receiving opening. 'Guiding' to the desired position means that the base plate is moved to a position wherein the user prefers the base plate to "sit" (be located) for (final/ensuing) adhesive attachment to the peristomal skin surface. The uptake portion primarily (but not exclusively, as it can continue to take up stomal effluents as long as it is not removed) performs its duty of taking up stomal effluents from the stoma and/or the peristomal skin surface during the guiding to the desired position. The base plate including the uptake portion is suitable for allowing the user to optionally provide a slight pressure to the distal surface of the carrier layer, when the base plate is in a desired position around the stoma to thereby optionally accelerate the uptake of stomal effluents, particularly mucin, from the peristomal skin surface to the uptake portion.

According to the first aspect, at least the uptake portion is adapted to be removed when the base plate is in a desired position around the stoma. This allows the user to remove the uptake portion having taken up the stomal effluents that was present on the stoma and/or on the peristomal skin surface and to subsequently attach the base plate to the peristomal skin without contamination of the adhesive material of the base plate having taken place. Thus, at least the uptake portion can be removed from the proximal surface of the adhesive material after having fulfilled its purpose of taking up stomal effluents to prevent contamination of the adhesive, and the thereby exposed (but uncontaminated) adhesive material can be applied (adhered) to the peristomal skin surface (typically the user will apply finger pressure on the distal surface of the base plate to ensure adhesion of the adhesive to the skin).

In embodiments, the removable protection element comprises at least a first segment and a second segment. In embodiments, the first segment is an innermost annular segment covering a centre portion of the base plate surrounding the stoma-receiving opening. In embodiments, the second segment is an outermost annular segment covering a peripheral portion of the base plate. In embodiments, the second outermost annular segment surrounds the first innermost segment. In embodiments, the first segment constitutes a first half of the removable protection element, such as, but not limited to, a first half covering the proximal surface of the adhesive material between a "12 (twelve) o'clock" and a "6 (six) o'clock" position. In embodiments, the second segment constitutes a second half of the removable protection element, such as, but not limited to, a second half covering the proximal surface of the adhesive material between a "6 (six) o'clock" and a "12 (twelve) o'clock" position.

In embodiments wherein the removable protection element comprises a first segment and a second segment, the uptake portion can advantageously be adapted to be removed (and is thus removable) together with the first segment of the removable protection element. Thereby, the uptake portion and the first segment of the removable protection element can be removed in a first removal step and the second segment of the removable protection element can be removed in a second removal step. Thus, a user can for example initially attach a surface portion of the adhesive material that has been exposed by removal of the uptake portion and the first segment (e.g. an innermost annular segment) of the removable protection element and ensure a good attachment of that surface portion of the adhesive to the peristomal skin surface before subsequently removing the second segment (e.g. an outermost annular segment) of the removable protection element and then attaching a second exposed portion of adhesive material ensuring a good attachment thereof to the skin. This inter alia provides for both a better (safer, by better adhesion) and easier attachment of the base plate to the peristomal skin surface because the user needs to control only smaller portions of exposed adhesive/sticky surface. The base plate of an ostomy appliance is often to be located at a difficult-to-access or difficult-to-see area of the skin surface. The handling of the product can therefore be easier for the user if only one (smaller) portion of adhesive is exposed at a time. This can be a particular benefit for users suffering from low dexterity or other motor disorders. It is to be understood that in embodiments the second segment of the removable protection element can be removed first, and the uptake portion can be removed with the first segment in a subsequent removal step. In other embodiments, the uptake portion is provided on both the first segment and the second segment of the removable protection element. Thereby, some of the uptake portion can be removed with the first segment of the removable protection element and a remainder of the uptake portion can be removed with the second segment of the removable protection element.

In embodiments, an entirety of the removable protection element is adapted to be removed when the base plate is in the desired position around the stoma. Thereby, the entire removable protection element and the uptake portion can be simultaneously removed in a single removal step providing for the proximal surface of the adhesive material to be entirely exposed and ready for adhesive attachment to the skin surface. This may be advantageous in some situations, e.g. in a training set-up wherein gaining knowledge of (or training) the manner of using the base plate according to the disclosure can be more important than ensuring the most optimal attachment and/or fit to the skin.

The removable protection element is provided on a proximal surface of the adhesive material which in turn is provided on a proximal surface of the carrier layer of the base plate. The removable protection element may cover the proximal surface of the adhesive material entirely or only partially. In embodiments, the base plate comprises at least one additional removable protection element.

In embodiments, the uptake portion covers an area corresponding to less than an entirety of an area of the adhesive material provided on the proximal surface of the carrier layer. In this manner, the uptake portion can be of limited extent, such as of limited radial extent and thus have a limited overall area in relation to an area of the removable protection element (and/or of the proximal surface of the adhesive material). In embodiments, the uptake portion can cover an innermost portion of the adhesive material of the base plate, the innermost portion extending partway from an inner periphery (edge) of the stoma-receiving opening radially towards an outer periphery (edge) of the base plate. In embodiments, the innermost portion can cover a range of between 5-75% of the total surface area of the adhesive material of the base plate, such as 10-60%, such as 20-50%, such as 30-40%. In embodiments, the uptake portion includes a flexible and/or elastic flange portion extending a flange distance radially inward from the inner periphery of the stoma-receiving opening. In embodiments, the flange distance can be in a range of 2-40 mm, preferably a flange distance of about 10 mm, preferably a flange distance of about 5-30 mm, such as 20-25 mm. In embodiments, the uptake portion is configured to cover at least an area corresponding to a cutting guide provided on the base plate (see otherwhere in this specification for a discussion of a cutting guide). In embodiments, the uptake portion is configured to cover an area corresponding to an annular cutting guide provided on the base plate+an additional radial extent of up to 10 mm, such as 5 mm. This is advantageous for example in providing an uptake portion that allows a user to cut along the widest extent of the cutting guide and still exhibits adequate uptake capacity. The size or extent of the uptake portion may inter alia depend on the specific type of stoma that is targeted by the base plate. Thus, the size or extent of the uptake portion can advantageously be selected to address specific needs for uptake of stomal effluents, e.g. such that for example a base plate for a urostomy is provided with an uptake portion provided on the proximal surface of the removable protection element that covers an entirety of the adhesive material on the proximal surface of the carrier layer because primarily liquid stomal effluents are targeted and therefore a large uptake capacity may be needed. For illustrative comparison, a base plate for a colostomy can then conversely be provided with an uptake portion that covers less than an entirety of the adhesive material, because then primarily solid stomal effluents are targeted (which would typically be less "runny" and hence easier to handle and control). It is, however, not to be understood that a colostomy necessarily produces less mucin than an ileostomy and/or a urostomy. The level of mucin generation is found to be individual from user to user. However, it has been shown is that an irritated stoma, e.g. a stoma in continuous contact with a base plate, appears to produce more mucin than is not irritated.

At least the uptake portion is suitable for taking up stomal effluents. In embodiments, the uptake portion comprises one or more materials suitable for taking up stomal effluents. In embodiments, the uptake portion comprises one or more structures suitable for taking up stomal effluents. In embodiments, the uptake portion comprises one or more materials and/or one or more structures suitable for taking up stomal effluents.

In embodiments, the uptake portion is provided by one or more absorbent powder(s) dusted onto a proximal surface of the removable protection element. In embodiments, the proximal surface comprises an adhesive coating or lining suitable for receiving and retaining such absorbent powder(s). In embodiments, the uptake portion is provided by lining, layering, spraying, or dusting an uptake capacity material onto a substrate of the removable protection element.

In embodiments, the uptake portion is configured to take up stomal effluents by absorption. In the present context this is to be understood such that the stomal effluents (solid, liquid and/or combinations thereof) are taken up by the volume of a bulk phase, e.g. the bulk of some solid material. Particularly, with respect to liquid stomal effluents, absorption primarily involves hygroscopy where water molecules are attracted and held in the volume of another (the bulk) material.

In embodiments, suitable materials for an uptake portion configured to take up stomal effluents by absorption, particularly but not exclusively by hygroscopy, include one or more of polymeric sheet material, a net (e.g. a polymeric net), a polymeric non-woven, a fabric, a pulp, a paper, a tissue, a textile, an open-celled memory foam, a Coloplast® BIATAIN® foam material (a hydrophilic, polyurethane open-celled foam material) or an integral foam material (also known as self-skin foam, a type of foam with a high-density skin and a low-density core). In embodiments, the uptake portion comprises an integral foam material and a surfactant. In embodiments, the uptake portion comprises a material made from a paper pulp. In embodiments, the uptake portion comprises a material made from a cellulose-based pulp.

Alternatively, or additionally, the uptake portion comprises one or more materials selected from hydrocolloids (such as, but not limited to, carboxy-methylcellulose (CMC) and potato starches), superabsorbent, minerals, gels, and sols.

In embodiments, the uptake portion comprises a combination, such as provided as a composite material, of, a structural component such as one or more of polymeric sheet material, a net (e.g. a polymeric net), a polymeric non-woven, a fabric, a pulp, a paper, a tissue, a textile, an open-celled memory foam, a Coloplast® BIATAIN® foam material or an integral foam material with one or more of a particulate or additive component such as hydrocolloids, superabsorbents, minerals, gels and sols. Providing an uptake portion as a combination or composite including one or more of the structural components and one or more of the particulate or additive components increases the uptake capacity of the uptake portion.

In embodiments, the uptake portion should have enough capacity to take up substantial amounts of urine, faeces, mucin (stoma juice) and other liquids including fresh and salty water (e.g. saline solutions) and soaps (e.g. residues from showering and other personal hygiene). "Substantial amounts" should be understood as the uptake portion having an uptake capacity of at least 50 (fifty) times its own weight per area or volume unit.

In embodiments, the uptake portion is configured to have an uptake capacity ranging from 0.005 g/30 s up to 10 g/30 s of stomal effluents. The inventors established by tests that a contamination of the adhesive material of a standard ostomy base plate from as little as 0.04 grams of liquid water applied within seconds caused a significant portion of the adhesive material's surface area to be affected and to have practically no adhesive capability or tack.

In embodiments, a thickness of the uptake portion varies in a range of 50μ-1000μ. It is to be understood that the range concerns the thickness before any uptake of stomal effluents.

A thickness in the lower end of the range provides a high degree of discretion and low bulkiness of the uptake portion and/or the removable protection element, whereas a thickness in the high end of the range provides superior uptake capacity.

In embodiments, a thickness of the removable protection element varies in a range of 50μ-1000μ.

In embodiments, the removable protection element is made from a polymeric sheet material having a thickness in a range of between 50μ-1000μ, and the uptake portion covers an area corresponding to less than an entirety of an area of the adhesive material provided on the proximal surface of the carrier layer, and the uptake portion is of greater thickness than the removable protection element.

In embodiments, the uptake portion is configured to take up stomal effluents by wicking. 'Wicking' is intended to include the act of moving moisture by capillary action. By taking up stomal effluents by wicking, e.g. using a suitable wick or wicking material, it is possible to protect the adhesive material of the base plate by removing the excess stomal effluents that gather on and around the stoma including on the peristomal skin surface and by wicking or channelling the taken-up effluents away from the adhesive material and the peristomal skin surface, thus reducing the risk of the effluents contaminating the adhesive material of the base plate. This is particularly, but not exclusively, advantageous in base plates for ostomy appliances that are used for collecting primarily or fully liquefied effluents, such as appliances for ileostomists and urostomists.

In embodiments, the wicking material is suitably a material that can transport stomal effluents from one location to another location. The wicking material is of a kind which absorbs and transports the effluents by relying on hygroscopy and/or capillary action, where the structure and the choice of wicking material ensures that the effluents can be taken up and transported in or by the material. In embodiments, the wicking material is an open-celled polymeric foam. In embodiments, the wicking material advantageously has a high transport capacity making it possible to distribute the wicking effect over an entirety of the uptake portion.

In embodiments, the uptake portion is configured to take up stomal effluents by containment. In such embodiments, the stomal effluents are taken up and held inside a containment material, which material typically is of a matrix-structure suitable for holding the effluents inside its structure. In embodiments, the uptake portion comprises a structure which is configured to take up and contain stomal effluents, but not to transport them.

In embodiments, the uptake portion is configured to take up stomal effluents by a combination of absorption and wicking.

In embodiments, the uptake portion is configured to take up stomal effluents by a combination of absorption and containment.

In embodiments, the uptake portion is configured to take up stomal effluents by a combination of wicking and containment.

In embodiments, the uptake portion is configured to take up stomal effluents by a combination of absorption, wicking, and containment.

In all the above identified combination embodiments, the respective combinations can apply one or more of the respective types of materials in combination with each other to achieve a combined and/or enhanced uptake effect.

In embodiments, the uptake portion and/or the removable protection element comprise(s) a liner or sheet material. In embodiments, the uptake portion and/or the removable protection element is/are provided as a sheet or sheet-like element. In embodiments, the uptake portion and/or the removable protection element is/are provided as a film or film-like element. In embodiments, the uptake portion and/or the removable protection element is/are made from one or more suitable materials for preparing liner, sheet, film, sheet-like or film-like materials. In embodiments, the materials include (but are not limited to) polymeric materials. In embodiments, the polymeric materials are chosen from polyethylene (PE), polypropylene (PP), polyurethane (PU), polybutylene, polyamide such as nylon, polyvinyl acetate, ethylene vinyl acetate, cellulose acetate or other thermoplastic polysaccharides, polyether block amides like PEBAX, block copolymers like styrene-isoprene-styrene block copolymers or ethylene acrylate block copolymers, polyesters such as polyethylene terephthalate (PET) or derivates thereof and/or combinations of such polymer materials.

In embodiments, the removable protection element is configured to be a release liner provided on the proximal surface of the adhesive material of the base plate. A release liner is a protective liner which covers the skin contacting side of the adhesive material, in order to ensure that the properties of the adhesive are preserved and that the proximal surface of adhesive material is not laid open until just before the use. In embodiments, the release liner is suitably a siliconized or fluorinated release liner, such as a siliconized or fluorinated craft paper, polyethylene, polypropylene, or polyethylene terephthalate film. It is understood that in such embodiments the release liner is siliconized or fluorinated on a surface adapted to be in contact with the adhesive material of the base plate (the siliconization/fluorination provides for easy release of the liner). In one embodiment, the release liner is a siliconized polyethylene film, such as medium density polyethylene from the company Huhtamdki located in Espoo, Finland. Such release liner allows for easy detachment of the removable protection element from the adhesive material on the proximal surface of the carrier layer when the removable protection element is to be removed. In embodiments, a distal surface of at least the uptake portion of the removable protection element comprises a release surface.

Alternatively, the removable protection element configured as a release liner can be a composite of e.g. a non-woven material and hydrocolloids, such as particulate hydrocolloids. In embodiments, the base plate can be understood to include a removable protection element which functions as both as a release liner protecting the adhesive e.g. during storage and transport, and as an additional component (in addition to the uptake portion) for eliminating stomal effluents and thereby avoid contamination of the adhesive material also during application of the base plate to the peristomal skin surface.

In embodiments, the uptake portion comprises a further protective liner on a proximal surface of the uptake portion. Particularly, but not exclusively, in embodiments in which the uptake portion is made from an absorbing material it comprises a further protective liner.

In embodiments, the uptake portion and/or the removable protection element is/are made from a composite material.

In embodiments, the uptake portion comprises an adhesive material. In embodiments, the removable protection element comprises an adhesive material. In embodiments, the uptake portion is formed from an adhesive material. In embodiments, the uptake portion is formed from a pressure-sensitive, hydrocolloid-containing adhesive material.

In the present disclosure, a composite material is to be understood as a material made from two or more constituent materials. In embodiments, the constituent materials may have significantly different physical and/or chemical characteristics that, when combined, yield a material with characteristics different from the individual components.

In embodiments, the uptake portion comprises a material dusted onto the proximal surface of the removable protection element. In embodiments, the removable protection element includes a substrate, such as a liner, sheet, film, sheet-like or film-like material made from polymeric material as discussed above, on a surface of which, a thin layer of adhesive material is applied (e.g. sprayed onto), and with a layer of hydrocolloids or other absorbents dusted onto the adhesive layer. Dusting absorbent material onto a surface of a substrate to create an uptake portion is an advantageous manner of providing a thin, discrete, and non-bulky uptake portion.

In embodiments, each of the uptake portion and/or the removable protection element comprise(s) at least one slit extending from a position at an inner edge of the uptake portion or the removable protection element defined by the stoma-receiving opening to a position on an outer peripheral edge of each of the uptake portion and/or the removable protection element. This allows for a user to remove either the uptake portion or the removable protection element or both from the base plate after the base plate has been guided to the desired position. As an illustrative example, it will be possible to remove the each of the uptake portion and the removable protection element with a protruding stoma extending through the stoma-receiving opening because of the at least one slit allowing the uptake portion and/or the removable protection element to be drawn off and removed, e.g. by performing a round-going movement around the stoma. In embodiments, the at least one slit of the uptake portion is aligned with the at least one slit of the removable protection element.

In embodiments, the at least one slit comprises a weakened line. In embodiments, a weakened line is a line created in the uptake portion and/or the removable protection element with a reduced material thickness compared to the material thickness of the rest of the uptake portion or protection element. In embodiments, the weakened line of the at least one slit is provided in the form of a kiss-cut or scored line in the uptake portion or protection element material. Providing the at least one slit as a weakened line can be advantageous in that the uptake portion or protection element can maintain a greater degree of "internal" integrity right until the moment where the uptake portion and/or protection element is/are to be removed by the user, thus providing support and/or reinforcement to the base plate construction right up to its application to the skin.

In embodiments, a first segment of the removable protection element is provided on (covers) a central portion around the stoma-receiving opening of the proximal surface of the adhesive material. In embodiments, a second segment of the removable protection element is provided on (covers) an outer peripheral portion of the proximal surface of the adhesive material. In embodiments, at least one slit separates a first segment of the removable protection element from a second segment of the removable protection element. In embodiments, at least one slit is provided annularly in the material of the removable protection element. Thus, in embodiments the removable protection element is separated in at least an inner segment and an outer segment separated by the annular slit.

In embodiments, the uptake portion and/or the removable protection element comprise(s) two slits. In one embodiment, a first and a second slit are provided linearly along an imaginary axis extending across the base plate and over the stoma-receiving opening. Thereby, the first and second slit can extend across the uptake portion and/or the removable protection element from a position at an inner edge of the removable protection element defined by the stoma-receiving opening to a position on an outer peripheral edge of the uptake portion and/or removable protection element. In other embodiments, at least a first slit and a second slit are provided at an angle to each other across the base plate (to be understood as an angle between two or more imaginary axis extending across the base plate and over the stoma-receiving opening).

In embodiments, the slit(s) is/are provided in a non-linear configuration, such as by extending across the uptake portion and/or the removable protection element from a position at an inner edge of the removable protection element defined by the stoma-receiving opening to a position on an outer peripheral edge of the uptake portion and/or removable protection element along a curve or arc. In embodiments, at least one slit is provided across the removable protection element in a spiral form or curve. This can be advantageous in that it allows a user to remove an outermost portion of the uptake portion and/or the removable protection element first and to thereby be able to attach an outermost portion of the proximal surface of the adhesive material before removing a remainder of the uptake portion and/or the removable protection element (by pulling on the spiral), thus providing control of attachment of the adhesive material while securing a low risk of adhesive material contamination.

In embodiments, the uptake portion and/or the removable protection element comprises three or more slits. Increasing the number of slits can be advantageous for example if the base plate is targeted for a patient having his/her stoma located in a particularly hard-accessible location on the body, or for other reasons, such as for purposes of training either users or health care professionals.

In embodiments, the at least one slit can alternatively or additionally be of curved, straight, spiral-shaped, concentric, polygonal, and other configurations. Combination of different configurations of the at least one slit, such as a slit having a first part of its extent as a straight segment and a second part as a curved segment, can also be implemented. Two or more slits can also be combined, e.g. provided in series one after another.

In embodiments, the at least one slit is through-going. "Through-going" is intended to mean that the slit(s) is/are cut entirely through the material of the uptake portion and/or the removable protection element. In embodiments, the slit(s) is/are partially through-going, i.e. some portions of the slit(s) are cut entirely through the material of the uptake portion and/or removable protection element whereas other portions of the slit(s) are not.

In embodiments, the uptake portion comprises a wafer. A "wafer" is to be understood as a small and thin disc or disc-like element. In embodiments, the wafer is provided as a separate (or individual) entity and configured to be attached to a proximal surface of the removable protection element, e.g. by an adhesive or other suitable means. A stoma-receiving opening can be provided before or after the uptake portion is attached to the removable protection element of the base plate. Embodiments of the uptake portion comprising a wafer are particularly, but not exclusively, advantageous when the uptake portion is configured to cover less than an entirety of the adhesive material provided on the proximal surface of the carrier layer. In embodiments, the uptake portion consists of a wafer.

In embodiments, the uptake portion covers an entirety of the proximal surface of the removable protection element and the removable protection element is provided on a centre portion of the proximal surface of the adhesive material immediately and annularly surrounding the stoma-receiving opening. A further release liner element is surrounding the uptake portion and covers a remainder of the proximal surface of the adhesive material of the base plate.

In embodiments, an uptake portion in the form of a wafer forms a separate or individual entity (or component) and is configured to be releasably attached to a proximal surface of the base plate, thereby forming an accessory (or accessory component) for the base plate for an ostomy appliance. In embodiments, the uptake portion in the form of a wafer is releasably attached to the proximal surface of the removable protection element.

In embodiments, the removable protection element comprises one or more cutting guides provided on a surface thereof, preferably at least on the proximal surface thereof.

In embodiments, at least a first cutting guide is provided on the removable protection element. In a general sense, a cutting guide is a line or curve or a pattern of lines or curves that is/are furnished on a surface of a base plate to assist a user in adapting the base plate to fit around his/her stoma, e.g. by cutting along such a line or curve. In embodiments, at least a first cutting guide is provided on one surface of the removable protection element. Alternatively, a cutting guide is provided on both surfaces of the removable protection element. In embodiments, the cutting guide(s) is/are printed onto the surface(s) of the removable protection element. Alternatives to printing the cutting guide(s) can be applied, such as, but not limited to, engraving and etching. Alternatively, a cutting guide can be integrated into the removable protection element. In one embodiment, the cutting guide is visible from one side of the removable protection element. In another embodiment, a cutting guide is visible from both sides of the removable protection element. In embodiments, a cutting guide is provided on a separate label which is configured to be adhered to a surface of the base plate, e.g. to the proximal surface of the removable protection element.

Additionally, or alternatively, cutting guide(s) can be provided on either surface (distal/proximal) of a wafer forming an uptake portion of the removable protection element. In embodiments, cutting guide(s) can be provided on either surface of a release liner covering the proximal surface of the adhesive material of the base plate. In embodiments, cutting guide(s) can be provided on more than one of the removable protection element, uptake portion, wafer, and release liner. In embodiments, a cutting guide can be provided on the carrier layer of the base plate. In embodiments, the cutting guide can be provided on a distal surface of the carrier layer of the base plate.

In embodiments, the cutting guide(s) is/are round. In embodiments, the cutting guide(s) is/are quadrangular. As an example, the cutting guide(s) is/are provided in a round or rounded shape which can be circular or elliptical or oval or approximating any of those shapes. In embodiments, 2-7 cutting guides are provided as predetermined shapes which are concentric with respect to the stoma-receiving opening and annular with respect to each other. In embodiments, a plurality of cutting guide(s) can be provided in a pattern. As an illustrative example, an initially provided stoma-receiving opening is round or circular in shape and a plurality of concentric circles distributed around the opening forms the cutting guides.

In embodiments, the cutting guide(s) comprise(s) an indication of the distance from a centre of the stoma-receiving opening and/or from the inner peripheral edge of the stoma-receiving opening to the one or more—such as each of—of the predetermined shapes. In embodiments, the predetermined shapes, such as concentric and annular lines, are provided in a pattern and equidistantly in relation to each other (and/or to the stoma-receiving opening). In embodiments, the predetermined shapes can be provided with a varying distance between individual shapes, such as with increasing or decreasing distance between each other.

In embodiments, the uptake portion is of greater thickness than the removable protection element. This can be advantageous inter alia for being able to target the base plate for a specific stoma application in that the thickness of the uptake portion can be increased for example to suit more exuding or "runny" stomas (e.g. including ileostomies and urostomies).

In embodiments, the uptake portion and/or the removable protection element comprise(s) means for facilitating removal of the uptake portion and/or the removable protection element from the base plate. In embodiments, the means for facilitating removal of the uptake portion and/or the removable protection element is provided as one or more ears or tabs. In embodiments, the means for facilitating removal is provided as one or more ears or tabs extending radially away from an outer peripheral edge of the uptake portion or the removable protection element or from an outer peripheral edge of each of the uptake portion and the removable protection element. In embodiments, at least one tab or ear is provided on each of the uptake portion and the removable protection element. In embodiments, the means for facilitating removal of the uptake portion and/or the removable protection element comprises at least one tab. The tab(s) is/are suitable for gripping by the fingers to remove the uptake portion and/or the removable protection element.

Alternative means for enabling easy grabbing and removal of the uptake portion and/or the removable protection element such as a portion of the uptake portion and/or the removable protection element having an increased thickness can also be applied. The means for facilitating removal can be an integrated part of the removable protection element and/or the uptake portion or alternatively be a separate part attached to the removable protection element and/or to the uptake portion thereof. In embodiments, the means for facilitating removal can be visually marked for example by a colour to guide the user to the correct location to grab and pull the removal means. Other suitable ways of marking the means for facilitating removal are acceptable.

In embodiments, the means for facilitating removal of the uptake portion and/or the removable protection element from the base plate is/are configured for removing an entirety of uptake portion and the removable protection element by one and the same removal action. In other words, all the removable protection element and the uptake portion is removed by one and the same removal action. The means for facilitating removal can be any one or more of the options described in embodiments above.

In embodiments, the uptake portion comprises a surfactant. In this disclosure, a surfactant is a substance which can reduce the surface tension of a liquid in which it is (or becomes) dissolved. In one embodiment, the surfactant comprises sodium laureth sulphate (also known as sodium lauryl sulphate or SLS). Other suitable surfactants are also acceptable, particularly anionic, and/or cationic surfactants. In one embodiment, the uptake portion comprises a polymeric net, such as a polyethylene-based net, and the polymeric net includes a surfactant, such as SLS, provided on surfaces of the net structure. Providing surfactant on the surfaces of a structural component of the uptake portion further enhances the uptake capability of the uptake portion and can also allow for an increased rate of the uptake of stomal effluents.

In embodiments, the removable protection element comprises a surfactant. In embodiments, only the uptake portion comprises a surfactant while the removable protection element does not comprise the surfactant. In embodiments, the uptake portion does not comprise a surfactant while the removable protection element comprises surfactant.

In embodiments, the removable protection element and/or the uptake portion comprises one or more other active substances or ingredients, including, but not limited to, substances for altering the viscosity of the stomal effluents by being releasable from the removable protection element or uptake portion in response to contact with the stomal effluents.

In embodiments, the uptake portion comprises an indicator. In embodiments, the indicator is a substance capable of indicating a reaction in the material of the uptake portion by a change in colour. Preferably, the indicator provides a significant (i.e. immediately visible) colour change in less than 10 seconds, such as preferably in less than 5 seconds. In embodiments, the indicator comprises one or more chromophores or chromophore groups. In embodiments, the indicator comprises a chromophore capable of yielding turquoise nuances. In embodiments, the indicator is a pH indicator. In embodiments, the indicator is a redox indicator. In embodiments, the indicator is provided in a plurality (at least two) of discrete zones which are distributed over the uptake portion. In embodiments, each one of a plurality of discrete zones is distributed on a proximal surface of the uptake portion. In embodiments, two or more indicators are comprised in the uptake portion. In embodiments, the removable protection element comprises an indicator. In embodiments, both the uptake portion and the removable protection element comprise an indicator. In embodiments, the indicator is a tactile indicator configured to provide a tactile sensation at least on the proximal surface of the uptake portion or the proximal surface of the removable protection element when exposed to stomal effluents. In embodiments, the indicator is a tactile and/or visual (e.g. capable of colour change) indicator provided on the proximal surface of the removable protection element and capable of indicating a contamination when exposed to stomal effluents. In embodiments, the tactile and/or visual indicator on the proximal surface of the removable protection element can indicate a reaction through the uptake portion. This could advantageously involve embodiments wherein the uptake portion comprises a polymeric net, tissue paper and/or other materials having a porous structure. In embodiments, the tactile indicator is configured to provide an increase in a thickness of the uptake portion where the tactile indicator is located. Alternatively, a decrease in the thickness.

In another, second aspect, the disclosure relates to an accessory for a base plate for an ostomy appliance. The accessory comprises a first structural component configured to be removably attached to a proximal surface of a base plate and a second uptake component provided on a proximal surface of the first structural component. Being provided "on a proximal surface" includes being permanently or temporarily or releasably attached to the proximal surface, e.g. by an adhesive. Alternatively, the second uptake component is integral with the first structural component and together comprised in the accessory. A stoma-receiving opening extends through the first structural component and the second uptake component. At least the second uptake component surrounds the stoma-receiving opening and is configured to take up stomal effluents. In embodiments, the first structural component of the accessory comprises a substrate, such as a liner, sheet, film, sheet-like or film-like material e.g. made from polymeric material as discussed in the first aspect. In embodiments, the second uptake component of the accessory comprises any one or more of the materials and structures described for the uptake portion of the first aspect of the disclosure.

In another, third aspect, the disclosure relates to a kit of parts. The kit of parts comprises a base plate for an ostomy appliance comprising a carrier layer, an adhesive material provided on a proximal surface of the carrier layer, a release liner provided on a proximal surface of the adhesive material, and, optionally, a first stoma-receiving opening in the base plate. The kit of parts further comprises an accessory comprising a first structural component configured to be attached to a proximal surface of the base plate, and a second uptake component provided integral with the first structural component or on a proximal surface of the first structural component. Being provided "on a proximal surface" includes being permanently or temporarily or releasably attached to the proximal surface, e.g. by an adhesive. Optionally, a second stoma-receiving opening is provided in the accessory. The characteristics and advantages of the individual components or elements of the kit of parts of the third aspect are the same as those described for the components of the first aspect of the disclosure. In embodiments, the kit of parts further comprises a collecting bag for collecting stomal effluents. In embodiments, the collecting bag is attached to a distal surface of the carrier layer. In embodiments, the collecting bag is permanently attached to the distal surface of the carrier layer (thereby forming a one-piece ostomy appliance). In embodiments, the collecting bag is releasably (detachably) attached to the distal surface of the carrier layer by inclusion of suitable coupling means (thereby forming a two-piece ostomy appliance). In embodiments, the kit of parts includes a set of instructions for use. In embodiments, the kit of parts further comprises a packaging. In embodiments, the packaging is configured to hold all the components (the individual parts) of the kit of parts. In embodiments, the kit of parts includes a plurality of accessories. This is particularly, but not exclusively, advantageous if the kit of parts is used in a training method or procedure conducted for users and/or for health care professionals. The training method or procedure concerns how to apply a base plate for an ostomy appliance without contaminating the adhesive material of the base plate during application according to aspects of the disclosure. In embodiments, the kit of parts includes a plurality of accessories.

In another, fourth aspect, the disclosure relates to a method for preventing contamination of an adhesive material of a base plate for an ostomy appliance during application of the base plate to the peristomal skin surface around a user' stoma. In one implementation, the method comprises the steps of:

i. providing a base plate according to the first aspect of the disclosure, and, optionally, customizing the stoma-receiving opening by cutting the opening to a preferred size and shape (thereby fitting the base plate with the user's stomal contour and/or personal preferences);
ii. providing the base plate in a peristomal skin position wherein the distal surface of the carrier layer faces away from the skin and wherein the stoma-receiving opening is engaged around the stoma;
iii. temporarily engaging the uptake portion with the peristomal skin surface by providing finger pressure on the distal surface of the carrier layer;
iv. removing the uptake portion, and, optionally, the removable protection element to expose at least a portion of the proximal surface of the adhesive material, and
v. securing the exposed portion of the proximal surface of the adhesive material to the peristomal skin surface.

Alternatively, or additionally to providing the finger pressure in step iii), the user can also perform a twisting or turning motion to the base plate to make the uptake portion turn on the peristomal skin surface in a wiping motion.

Suitable approaches to securing the exposed portion of adhesive material to the peristomal skin surface include using finger pressure, uv-radiation, heat application, swiping with a moist cloth on the distal surface of the base plate and/or combinations thereof. The customization by cutting according to step i) of the procedure is optional in that a stoma-receiving opening is often provided in the base plate at manufacture, and can therefore already be suitable for the individual user's needs when delivered, whereas in many cases the user may need to further adapt or customize a "standard" stoma-receiving opening to his or her individual stoma shape and preferences.

It has been found by repeated trial runs that, if the above described method according to the fourth aspect is followed, the risk of contaminating the adhesive material of the base plate during application to the peristomal skin surface around a stoma can be significantly reduced or even eliminated. This is because the uptake portion takes up the contaminating stomal effluents as the user provides the base plate in a position on, near or adjacent the peristomal skin surface (but not yet actively attached thereto) and in engagement with the stoma—any stomal effluents coming into contact with the surface(s), including the proximal surface of the adhesive material of the base plate, are taken up when the base plate is in the peristomal skin position. When the base plate is in a desired position to the satisfaction of the user, at least the uptake portion (having taken up the damaging stomal effluents during the positioning) is removed from the base plate. Thereby, at least a portion of the proximal surface of the adhesive material is exposed and ready for attachment (for being adhered) to the peristomal skin surface without the adhesive material having been contaminated before its contact with the skin. Immediately thereafter, the exposed portion of the adhesive material is secured (adhered) to the peristomal skin surface by one of the suitable approaches described above. The base plate is thereby attached (adhered) to the skin surface by the adhesive material without this having been compromised already from the beginning of its "life" on the user's skin. Following the method according to the fourth aspect is found to increase the overall accomplishable wear time of the base plate because the adhesive material is in optimal condition and has optimal conditions for functioning as it is designed to at the beginning of its lifespan.

In embodiments of the method, wherein the user removes the uptake portion only in a first removal action, he or she can subsequently remove the removable protection element in a second removal action.

In embodiments, step iv) of the method according to the fourth aspect comprises removing both the uptake portion and the removable protection element to expose an entirety of the proximal surface of adhesive material.

Particularly, but not exclusively, the uptake portion and/or the removable protection element with the uptake portion provided on its proximal surface comprise(s) at least one slit extending from a position at an inner edge of the uptake portion and/or the removable protection element defined by the stoma-receiving opening to a position on an outer peripheral edge of the uptake portion and/or the removable protection element, as described above with respect to the first aspect. Particularly, but not exclusively, the uptake portion and/or protection element is removed by the user pulling on one or more means for facilitating removal, such as, but not limited to one or more tab(s) or ear(s) provided on or attached to the uptake portion and/or to the removable protection element. This causes each of or both of the uptake portion and/or the removable protection element to separate or disunite along each of the at least one slits. This in turn ensures that the uptake portion and/or the removable protection element can be removed without difficulty by the user guiding and/or directing the uptake portion and/or protection element either clockwise or counter clockwise around the stoma thereby releasing the uptake portion and/or protection element from the base plate, and consequently thereby also removing stomal effluents taken up by the uptake portion. In other implementations of the method, the uptake portion and/or the removable protection element each includes more than one slit, e.g. two slits dividing the uptake portion and/or protection element in two halves or other segments (e.g. innermost and outermost segments), and the user can then alternatively remove one half or segment at a time. This further facilitates correct positioning and security of the base plate against stomal effluent contamination in that it allows the user to concentrate on a stepwise securing (subsequent adhesive attachment) of smaller portions of adhesive material to the peristomal skin.

In embodiments, the uptake portion and/or the removable protection element can be provided as a wafer as described for the first aspect. Step i) of the method of preventing contamination of the adhesive according to the fourth aspect can then advantageously include a further step of attaching the wafer to a proximal surface of the base plate. In embodiments, the method can further include a step of attaching a cutting guide provided on a label to the proximal surface of the removable protection element and/or to the wafer before attaching the wafer.

In embodiments, the method according to the fourth aspect can further include a step i.b) which includes applying a releasable stoma cover over the user's stoma using an applicator and a releasable stoma cover. A suitable releasable stoma cover is disclosed in applicant's publication WO2019/141324. The releasable stoma cover includes a hood-like element including a proximal end portion and a distal end portion. The releasable stoma cover is defining a generally longitudinal direction between the first and the second end portions. The proximal end portion of the hood-like element is configured to be adjustable at least in a direction transverse to the longitudinal direction. This provides inter alia for a stoma entrance of the stoma cover to be of variable size. The distal end portion of the hood-like element is configured as a closed end portion. There is no stoma entrance or similar opening in the closed distal end portion of the hood-like element. The term "releasable" should be understood in relation to the stoma cover being able to be released from the applicator. The stoma cover is suitably removed in a step v) according to the method. In embodiments, however, the stoma cover and the removable protection element can be removed simultaneously in step iii). Applying such a stoma cover is advantageous and useful in that it additionally greatly reduces any likelihood of soiling the user's fingers and/or components, including the adhesive material of a new base plate to be applied during appliance exchange. In a method according to the fourth aspect, performing an additional step of applying a stoma cover for protection during application of the base plate and a subsequent step of removing the stoma cover after attachment of the base plate to the peristomal skin surface, further helps to increase security against contamination of the adhesive material.

In another, fifth aspect, the disclosure relates to a method for training a user of an ostomy appliance to prevent contamination of an adhesive material of a base plate of the ostomy appliance during application of the base plate to the peristomal skin surface around a user's stoma. In one implementation, the method comprises the steps of:

a. providing a base plate according to the first aspect of the disclosure, and, optionally, customizing the stoma-receiving opening by cutting the opening to a preferred size and shape (fitting with the user's stomal contour and/or personal preferences);
b. providing the base plate in a peristomal skin position wherein the distal surface of the carrier layer faces away from the skin and wherein the stoma-receiving opening is engaged around the stoma;
c. temporarily engaging at least the uptake portion with the peristomal skin surface by providing finger pressure on the distal surface of the carrier layer;
d. withdrawing the base plate from the peristomal skin surface position;
e. inspecting the uptake portion to assess location and amount of taken-up stomal effluents on the uptake portion and, optionally, recording data relating to the assessment.

If stomal effluents have also contaminated the removable protection element radially outward of the uptake portion, data relating to such contamination can additionally be recorded. Alternatively, or additionally to providing the finger pressure in step c), the user can also perform a twisting or turning motion to the base plate to make the uptake portion turn on the peristomal skin surface in a wiping motion.

If the method according to the fifth aspect of the disclosure is followed, a user and/or a health care professional can train the use of a base plate according to the disclosure and it is believed that they thereby can train and learn how to significantly reduce or even eliminate the risk of contaminating the adhesive material of a base plate during application to the peristomal skin surface around a stoma. By following the method, and particularly by carrying out step e), the user can get an impression of the amount and character of the contamination of the adhesive material of the base plate from the stomal effluents. As discussed for the first aspect, this can be a contamination that is otherwise often not noticed and/or which is not at the forefront of a user's mind when applying a fresh base plate and having cleansed and wiped the stoma and peristomal area clean e.g. with tissue paper (in the user's eyes apparently clean). Not only is the method advantageous for illustrating such contamination to a user, it can also be beneficial in teaching the user where on the surface of the adhesive material contamination most frequently occurs. These learnings can be obtained by carrying out repeated cycles of the training method according to the fifth aspect whereby the user is educated about how to apply the base plate is an optimal manner and also where to be particularly careful when applying the base plate (e.g. where on and adjacent the stoma problems tend to occur). Moreover, these learnings pave the way for the user to take further precautionary measures to avoid compromising the adhesive material's tack etc., such as adding an extra amount of adhesive, e.g. of an accessory adhesive paste, to the location(s) on the adhesive surface of the base plate in which the user has had the contamination illustrated by carrying out the method. This can further help reducing the likelihood of leakage and increase the user's confidence and quality of life.

The user's learnings are facilitated because the uptake portion takes up the potentially contaminating stomal effluents as the user applies the base plate and provides it in a desired peristomal skin position and with the stoma-receiving opening in engagement with the stoma—any stomal effluents are taken up by the uptake portion as the base plate is guided to the desired peristomal skin surface position.

After the base plate has been positioned in the desired peristomal skin surface position around the stoma, at least the uptake portion is temporarily engaging the peristomal skin surface by providing finger pressure on the distal surface of the carrier layer of the base plate. This helps to further ensure that the stomal effluents coming into contact with the uptake portion are taken up thereby, and/or providing at least an illustrative and/representative print or mark or "impression" of the stomal effluents on or in the uptake portion.

Subsequently, the base plate can then be withdrawn or removed carefully from the peristomal skin position and free of engagement with the stoma. This allows for the user to inspect the uptake portion to assess a location and amount of taken-up stomal effluents on the uptake portion (and/or on the removable protection element). If needed, the method further optionally includes to record data relating to the assessment. Various assessment and evaluation approaches can be applied. These can include visual inspection, tactile examination or palpation of the contaminated areas (or of portions of the distal surface of the base plate corresponding to where the effluents are taken up), weighing of the base plate or the uptake portion, moisture content determination using appropriate measuring tools and other. Combinations of assessment methods are also possible. In the event an optional step of data recording is carried out, collected data can advantageously be stored and used e.g. for future customization of base plates and ostomy appliances for the individual user, particularly for optimizing the structure and materials of the uptake portion and/or the removable protection element.

In some implementations, the uptake portion comprises an indicator as described above for the first aspect. For example, the indicator is a substance capable of indicating a reaction in the material of the uptake portion by a change in colour. A change in colour can for example take place in portion(s) of the uptake portion that has/have taken up stomal effluents. This is advantageous in that is assists the user in an easy determination not only of where the effluent problems may typically occur, but also whether the user has been adequately mindful to provide finger pressure on the distal surface of the carrier layer of the base plate, which is another advantage of the method according to the fifth aspect. When the base plate is subsequently attached to the peristomal skin surface by means of the adhesive material, it is further important for an optimal adhesion that the user provides adequate finger pressure on the distal surface of the base plate corresponding to the area of adhesive material on the proximal surface, particularly, but not exclusively, in the central portion of the adhesive closest to the stoma. The better the compliance in pressing the adhesive material into contact with the peristomal skin surface, the better adhesion and thus security against leakage seeping in between the adhesive material and the skin surface. Applying an uptake portion including an indicator can therefore further help to illustrate to the user if there are areas of the base plate where more finger pressure should be applied to ensure the attachment. This is particularly useful in a training situation and thus particularly, but not exclusively, in the method according to the fifth aspect of the disclosure. Further, this provides an incentive for the user to train the application of the base plate to the peristomal skin surface in that an illustrative and intuitive feedback on what to improve during application of the base plate is immediately provided to the user.

In embodiments of the fifth aspect, a colour indicator can be provided in or on the proximal surface of the adhesive material. Thereby, in the training setting, a user training the application of a base plate according to the disclosure can further gain learning from looking at the adhesive of the base plate after having removed the uptake portion and/or the removable protection element to experience whether or not there is still stomal effluents on the peristomal skin surface. If so, the user can see this as a change in colour by the colour indication in/on the adhesive material. Thereby, the user can further train to optimize the positioning of the base plate around the stoma and the removal of the uptake portion and/or the removable protection element according to the disclosure. Providing a colour indicator in the uptake portion and in or on the adhesive material can therefore provide an educational tool for visualizing an otherwise unnoticeable contamination of the proximal surface of the adhesive material of the base plate.

Steps of assessment and data recording can also be incorporated in the method of preventing contamination according to the fourth aspect of the disclosure.

In embodiments, the method according to the fifth aspect further comprises the steps of:

f. providing the base plate in the peristomal skin surface position anew;
g. removing the uptake portion and, optionally, the removable protection element to expose at least a portion of the proximal surface of the adhesive material;
h. securing the exposed portion of the proximal surface of the adhesive material to the peristomal skin surface.

In some implementations of the method according to the fifth aspect, the order of steps f) and g) can be reversed such that the uptake portion and optionally the removable protection element is removed (step g) before re-applying the base plate to the peristomal skin surface anew (step f). In one implementation, this reversed approach can be applied if the re-positioning of the base plate is carried out immediately after inspection and removal of the uptake portion, such that no new stomal effluents have generated on the stoma and/or on the peristomal skin surface. Steps g) and h) are carried out in a manner similar to steps iv) and v) of the method of preventing contamination according to the fourth aspect.

In embodiments of the method according to the fifth aspect, the uptake portion is provided as a wafer as described for embodiments of the first aspect. Step i) of the method of preventing contamination of the adhesive according to the fifth aspect can then advantageously include a further step of attaching the wafer to a proximal surface of the removable protection element.

In embodiments, the method can further include a step of attaching a cutting guide provided on a label to the proximal surface of the protection element and/or to the wafer before attaching the wafer.

In embodiments, step g) of the method according to the fifth aspect comprises removing both the uptake portion and the removable protection element to expose an entirety of the proximal surface of adhesive material.

In embodiments, wherein the user removes solely the uptake portion in a first removal action, he or she can subsequently remove the removable protection element in a second removal action.

DETAILED DESCRIPTION OF THE DRAWINGS

FIG. 1 is a schematic view of one embodiment of a base plate 20 for an ostomy appliance 10. The base plate 20 combines with a collecting bag 15 to form the ostomy appliance 10. Also shown in FIG. 1 is a schematic indication of a user's stoma S and a surrounding peristomal skin surface P.

Figure 2A:
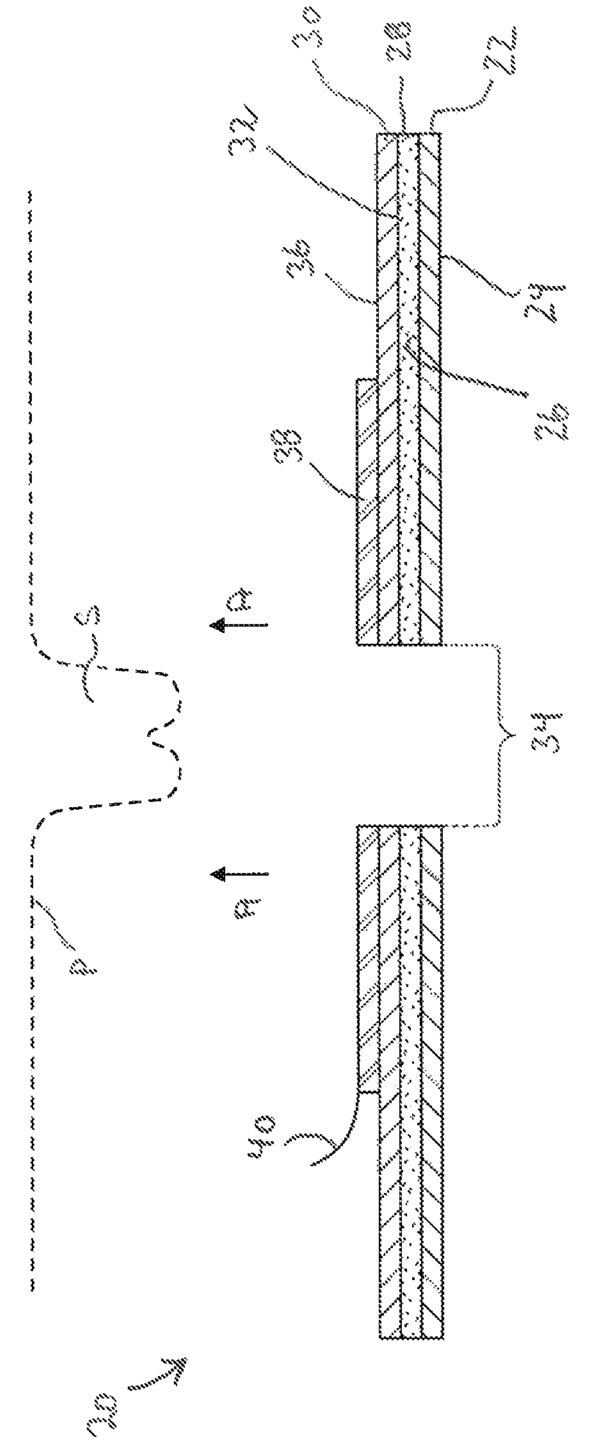
FIG. 2A is a cross-sectional view of one embodiment of a base plate for an ostomy appliance.

FIG. 2A is a cross-sectional view of one embodiment of a base plate 20 for an ostomy appliance 10 according to the disclosure. A schematic indication of a stoma S and the surrounding peristomal skin surface P of a user is provided in dotted line. The arrows A indicate the direction for moving the base plate 20 to a desired position adjacent the peristomal skin surface P around the stoma S.

The base plate 20 includes a carrier layer 22 having a distal surface 24 and a proximal surface 26. An adhesive material 28 is provided on the proximal surface 26 of the carrier layer 22 and is adapted for adhering the base plate 20 to the peristomal skin surface P around the stoma S of the user. A removable protection element 30 is provided on a proximal surface 32 of the adhesive material 28. A stoma-receiving opening 34 extends through the carrier layer 22, the adhesive material 28 and the removable protection element 30.

An uptake portion 38 is provided on a proximal surface 36 of the removable protection element 30 and surrounds the stoma-receiving opening 34 and is configured to take up stomal effluents to prevent the adhesive material 28 from being contaminated by stomal effluents as the base plate 20 is guided to a desired position adjacent the peristomal skin surface P with the user's stoma S engaging the stoma-receiving opening 34. 'Guiding' to the desired position means that the base plate 20 is moved to a position wherein the user prefers the base plate to "sit" (be located) for the ensuing adhesive attachment to the peristomal skin surface P. The uptake portion 38 is adapted to be removed when the base plate 20 is in position in the desired peristomal skin position around the stoma S. In the illustrated embodiment, a tab (or ear) 40 is further shown provided on the uptake portion 38. The tab 40 is suitable as a means for facilitating removal of the uptake portion 40 from the removable protection element 30. It is also possible to provide one or more tabs in locations on the removable protection element 30. In FIG. 2A, the base plate 20 is shown some distance away from the peristomal skin surface P and the stoma S.

The uptake portion 38 primarily performs its duty of taking up stomal effluents during the guiding to the desired position but continues to do so as long as it is not removed from the base plate 20. The user can optionally provide a slight finger pressure (FP, see FIG. 2C) to the distal surface 24 of the carrier layer 22, when the base plate 20 is in the desired peristomal skin position around the stoma S to thereby optionally accelerate the uptake of stomal effluents 46, particularly mucin from the peristomal skin surface P to the uptake portion 38.

Figure 2B:
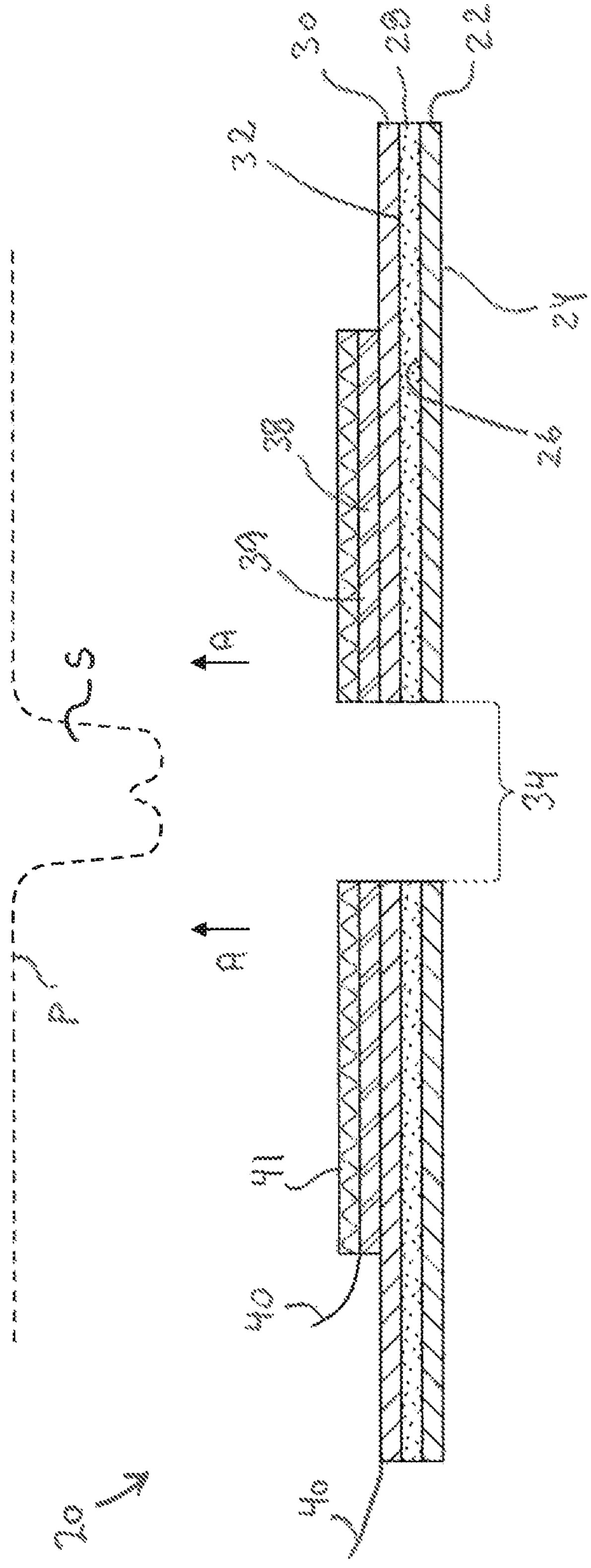
FIG. 2B is a cross-sectional view of one embodiment of a base plate for an ostomy appliance corresponding to the one illustrated in FIG. 2A.

FIG. 2B is a cross-sectional view of an embodiment of the base plate 20 corresponding to the one illustrated in FIG. 2A, however, including a further protective liner 41 protecting the uptake portion 38 until use. Although not shown in the figures, the protective liner 41 can itself include at least one tab for removal. Similarly, the removable protection element 30 can include one or more tabs 40.

Figure 2C:
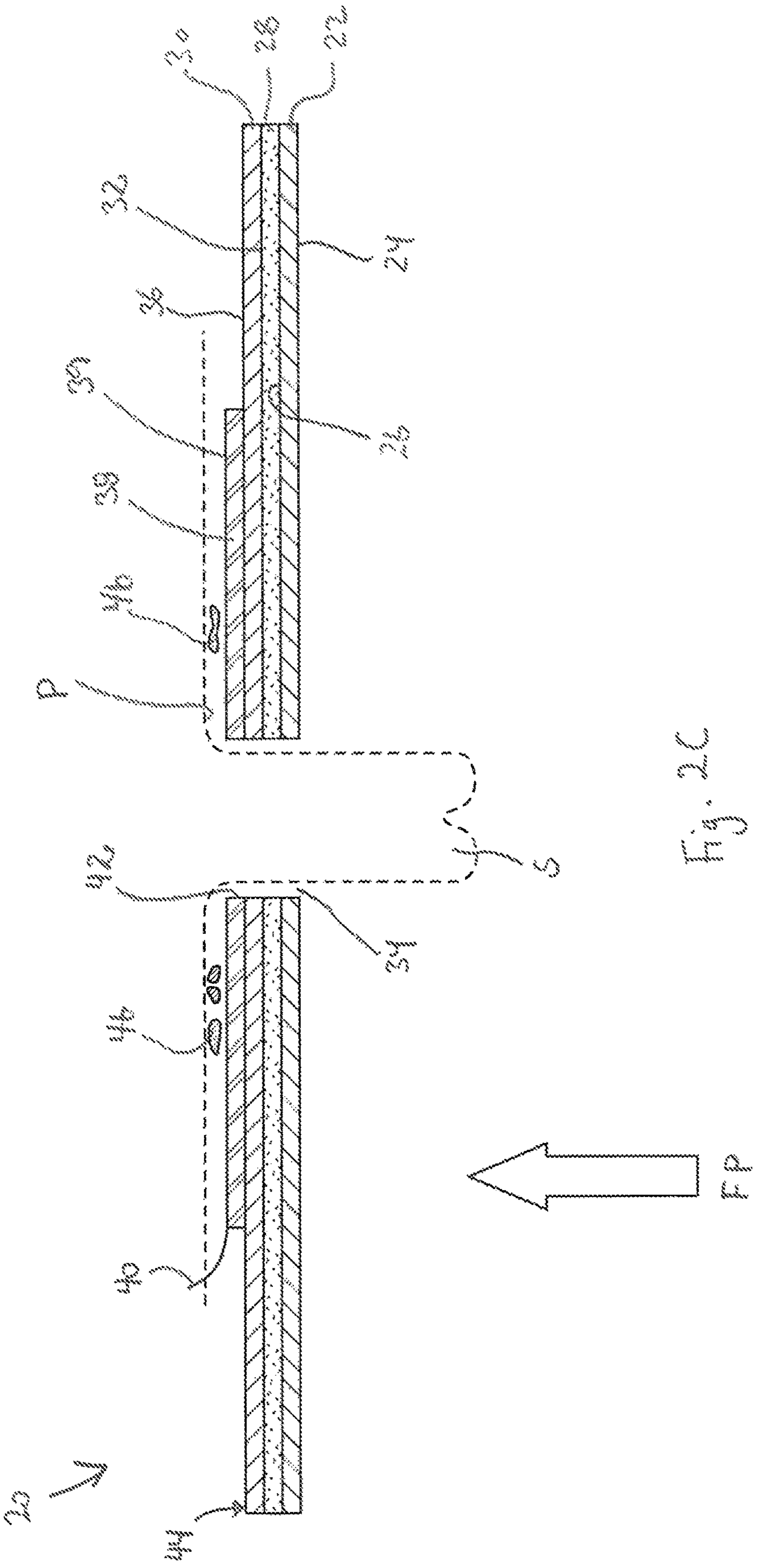
FIG. 2C is a cross-sectional view of one embodiment of a base plate for an ostomy appliance corresponding to the one illustrated in FIG. 2A.

FIG. 2C is a cross-sectional view of an embodiment of the base plate 20 corresponding to the one illustrated in FIG. 2A, however, in FIG. 2C the protective liner 41 has been removed and the base plate 20 has been moved in the direction of the arrows A (FIG. 2A) to a desired position adjacent the peristomal skin surface P with the user's stoma S engaging the stoma-receiving opening 34. The uptake portion 38 is thereby available to take up stomal effluents 46 from the peristomal skin surface P. The uptake of effluents 46 can be further accelerated by the user providing finger pressure to the distal surface 24 of the carrier layer 22, as indicated by arrow FP.

In the embodiments illustrated in FIGS. 2A, 2B and 2C, the uptake portion 38 is provided on the proximal surface 36 of the removable protection element 30 such that the uptake portion 38 covers an area corresponding to less than an entirety of an area of the adhesive material 28. In the illustrations, the uptake portion 38 covers an area of adhesive material 28 surrounding the stoma-receiving opening 34 and extends radially outward therefrom to a position at approximately half the distance between an inner peripheral edge 42 of the stoma-receiving opening 34 and an outer peripheral edge 44 of the base plate 20. The uptake portion 38 therefore also extends over less than an entirety of the proximal surface 36 of the removable protection element 30.

Figure 3:
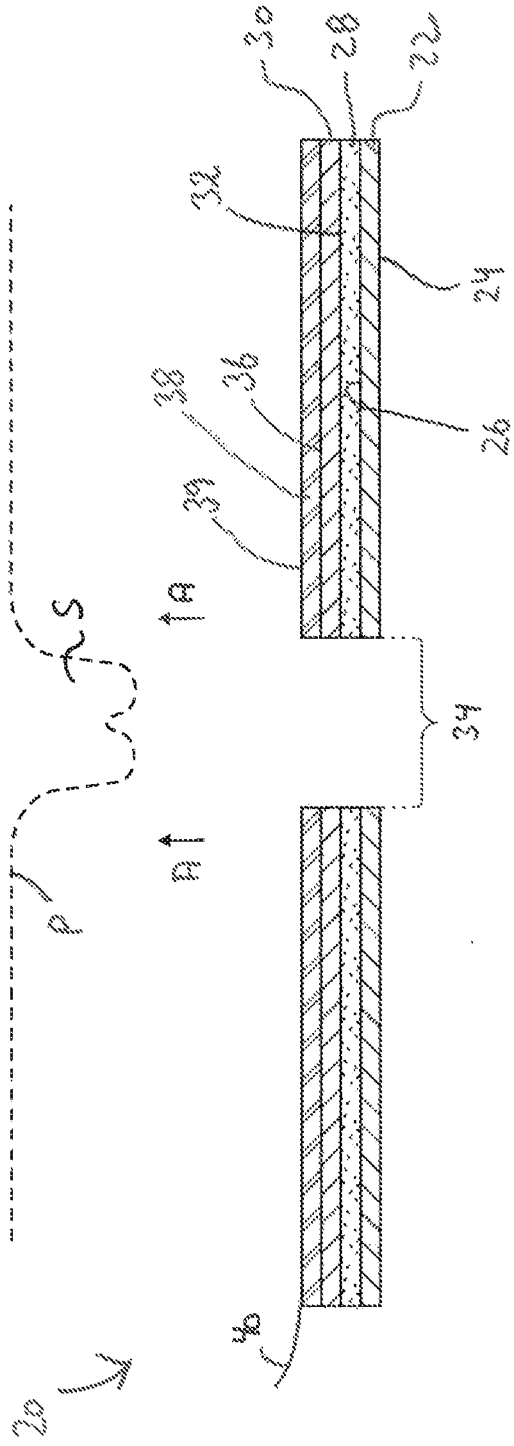
FIG. 3 is a cross-sectional view of one embodiment of a base plate shown in the same position as the base plate in FIGS. 2A and 2B.

FIG. 3 is a cross-sectional view of one embodiment of a base plate 20 shown in the same position as the base plate in FIGS. 2A and 2B. In the embodiment of FIG. 3, the uptake portion 38 covers an area corresponding to an entirety of the area of the adhesive material 28. In the illustration of FIG. 3, the uptake portion 38 surrounds the stoma-receiving opening 34 and extends radially the entire distance between an inner peripheral edge 42 of the stoma-receiving opening 34 and an outer peripheral edge 44 of the base plate 20. The uptake portion 38 therefore also extends over an entirety of the proximal surface 36 of the removable protection element 30. The uptake portion 38 includes a proximal surface 39. Although not shown in FIG. 3, it is to be understood that the uptake portion 38 in FIG. 3 can also include a further protective liner 41 (FIG. 2B) provided on the proximal surface 39 of the uptake portion 38. FIG. 3 further illustrates a tab 40 provided on the uptake portion 38 facilitating removal.

In the embodiments illustrated in FIGS. 1-3, the stoma-receiving opening 34 is shown to be provided in a centre portion of the base plate 20. However, it should be understood that the stoma-receiving opening 34 can be provided radially offset from a centre portion of the base plate 20.

In the embodiments illustrated in FIGS. 2 and 3, the uptake portion 38 is releasably adhered to the proximal surface 36 of the removable protection element 30. In FIGS. 2 and 3 a thin layer or coating of a suitable weak adhesive (not shown) is provided on either a distal surface of the uptake portion 38 or on a proximal surface 36 of the removable protection element 30. In these embodiments, the uptake portion 38 is removable independently of the removable protection element 30, such as by a first removal action, and the removable protection element 30 is separately and independently removable, such as by a second removal action.

Figure 4:
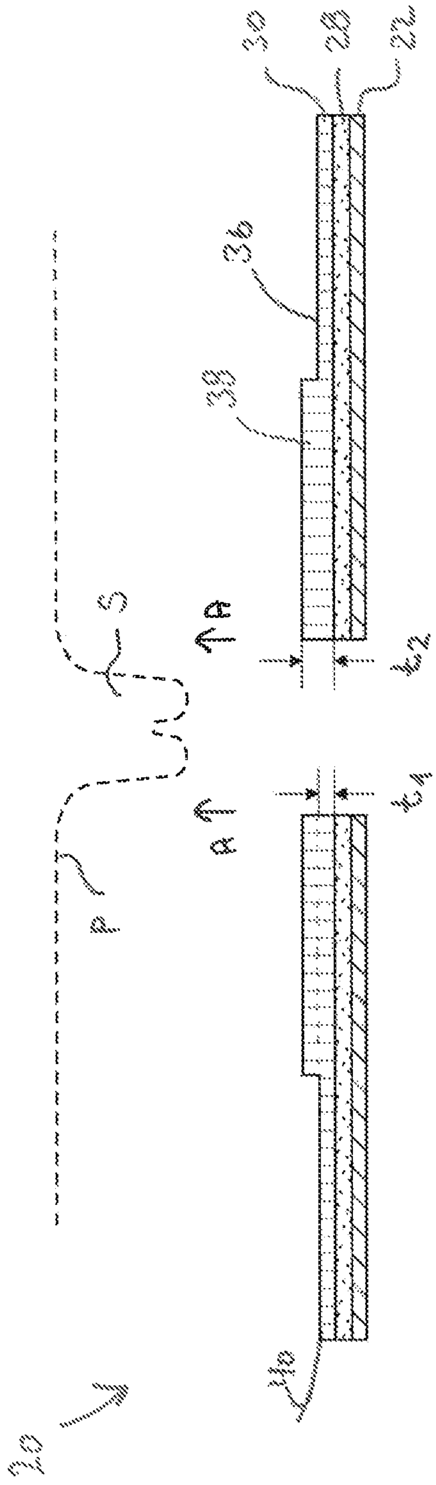
FIG. 4 is a cross-sectional view of one embodiment of a base plate for an ostomy appliance.

In the embodiment illustrated in FIG. 4, the uptake portion 38 is integral with and forms at least a portion of the proximal surface 36 of the removable protection element 30. In the embodiment of FIG. 4, the uptake portion 38 cannot be separated from the removable protection element 30 without one or both being destroyed and/or losing their functionality. An entirety of the removable protection element 30 including the integrated uptake portion 38 can be removed in one and the same removal action by pulling on the at least one tab 40. FIG. 4 further shows that the uptake portion 38 is of greater thickness t2 than the thickness t1 of the removable protection element 30.

Figure 5:
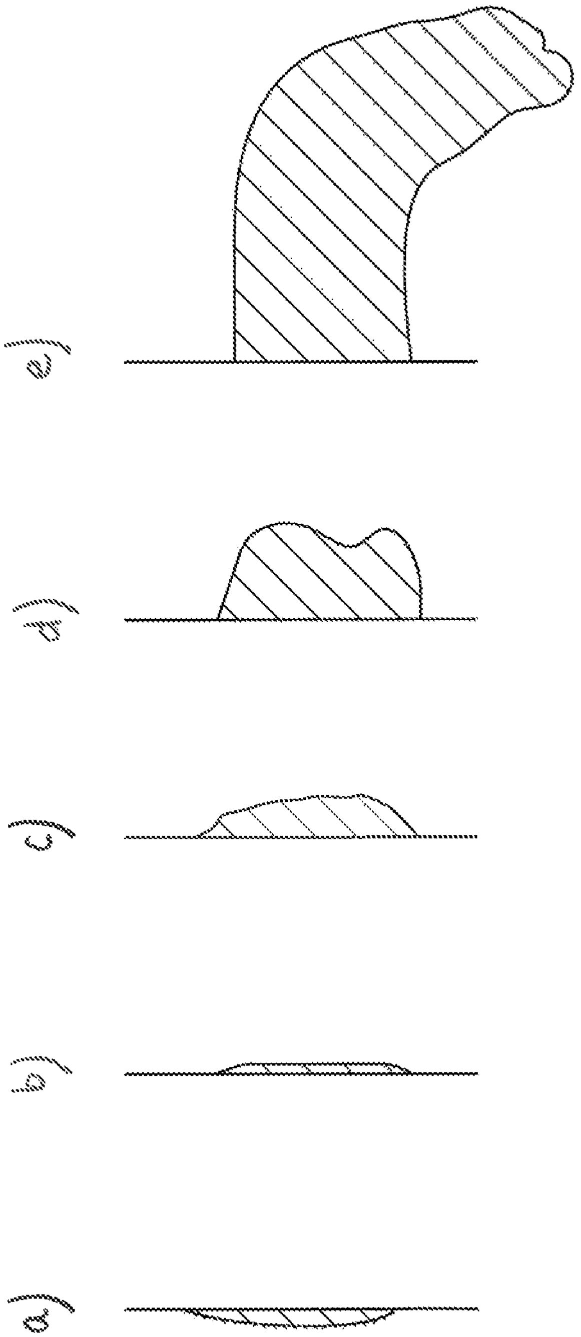
FIG. 5 is a schematic illustration of five different stoma profiles.

FIG. 5 is a schematic illustration of five different stoma profiles that are representative, but not exhaustive, for a stoma population and addressed by the invention. Stoma a) is identified as a retracted stoma; stoma b) as a flush stoma; c) as a low-profile stoma; d) as a protruding stoma and e) as a prolapsing stoma. The engagement between the stoma-receiving opening 34 of a base plate 20 according to the disclosure and a user's stoma can be with any of the shown stoma profiles and achieve the advantages of the disclosure.

Figure 6C:
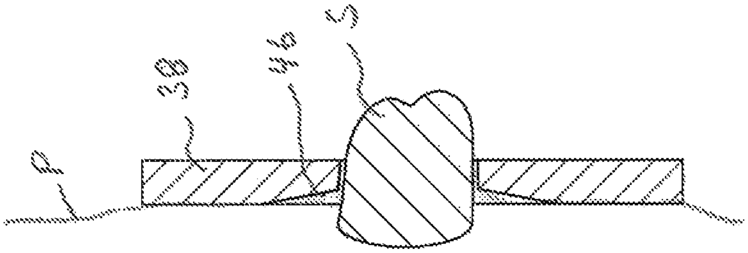
FIGS. 6A-6C are schematic drawings showing a user's stoma S and peristomal skin surface P.
Figure 6B:
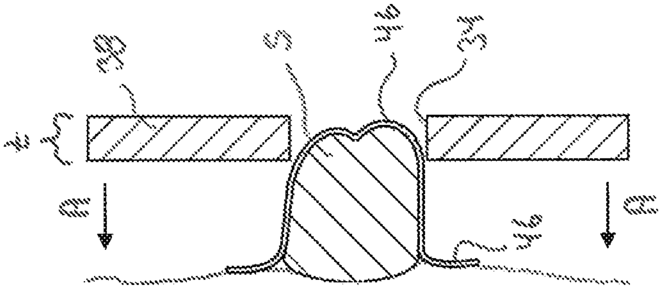
Figure 6A:
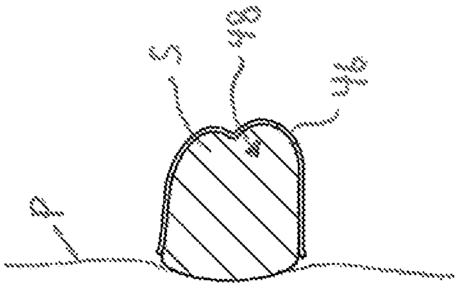
Figure 9:
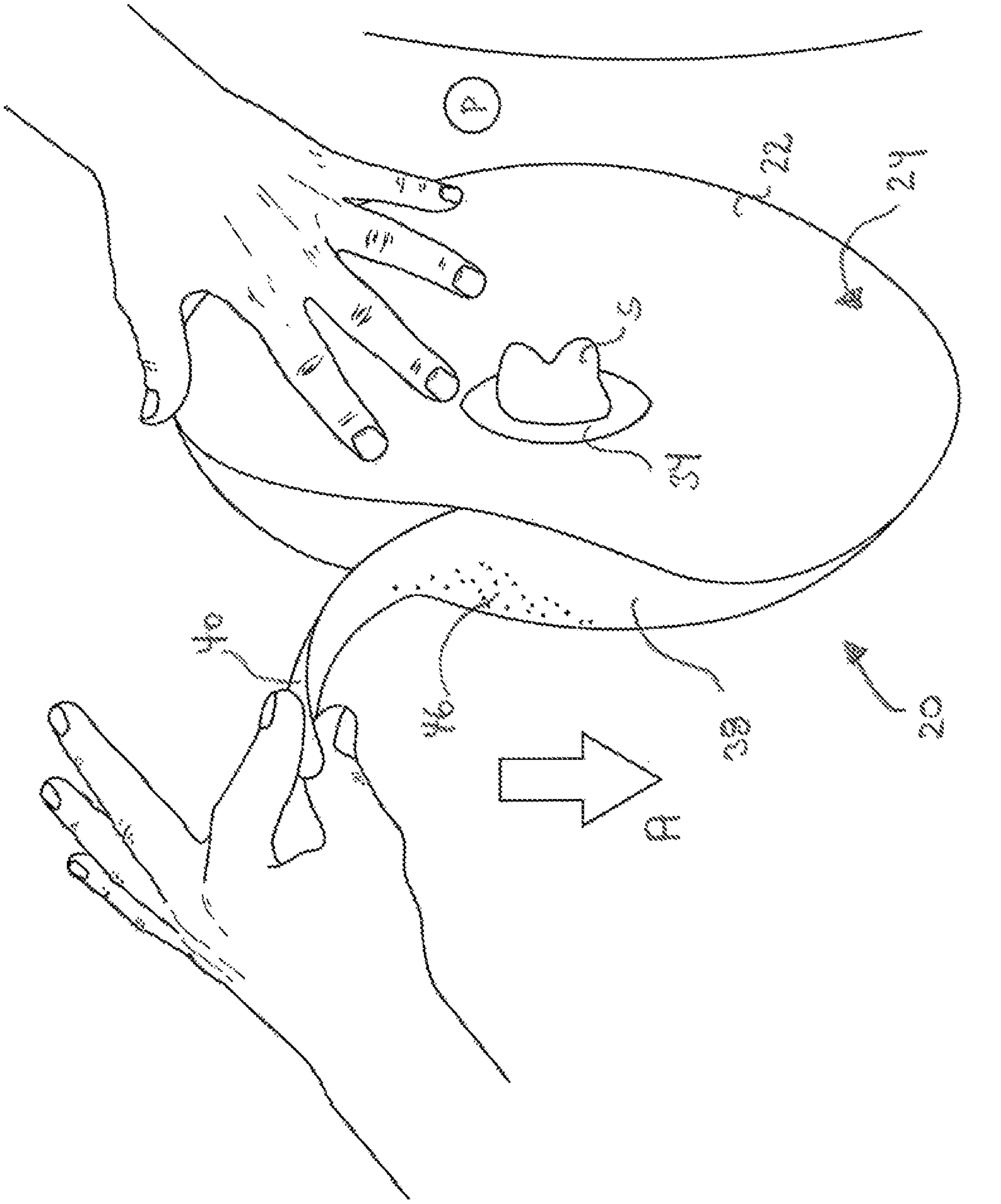
FIGS. 9A-9B are both reproductions of photos taken during a test and are presented to further illustrate the problem of stomal effluents contaminating the adhesive of an ostomy appliance base plate.

In FIGS. 6A-6C, the uptake portion 38 is configured to take up stomal effluents 46, particularly mucin, which seeps from the surface of the stoma S and/or have contaminated the peristomal skin surface P around the stoma S. In FIGS. 6A-6C, the mucin 46 is indicated by a dark colour. It is important to note that in real life the mucin 46 is practically unnoticeable to the eye (transparent or clear). However, for the sake of illustrating principles of the invention in FIGS. 6A-6C, the mucin 46 is coloured dark.

FIG. 6A is a schematic drawing showing a user's stoma S and peristomal skin surface P and with an indication in dark colour of stomal effluent 46 in the form of mucin being formed on the surface 48 of the stoma S.

FIG. 6B is a schematic drawing showing an uptake portion 38 of a base plate (not shown) being guided in the direction of the arrows A to a desired position adjacent the peristomal skin surface P with the user's stoma S engaging the stoma-receiving opening 34 and with an indication in dark colour of stomal effluent 46 in the form of mucin being formed on the surface 48 of the stoma S and also have begun seeping onto the peristomal skin surface P. The thickness t of the uptake portion 38 is exaggerated for illustration.

FIG. 6C is a schematic drawing showing the uptake portion 38 in the desired position adjacent the peristomal skin surface P with the user's stoma S engaging the stoma-receiving opening 34. Stomal effluent 46, at least in the form of mucin, on the peristomal skin surface P, and in some cases also from the stoma surface 48, is shown to being taken up by the uptake portion 38. The taken-up stomal effluents 46 are removed with and when the uptake portion 38 is removed from the peristomal skin surface P by the user.

FIG. 7 is a schematic, perspective view of one embodiment of a base plate as disclosed herein. FIG. 7 illustrates the base plate 20 having been guided to a desired position on a peristomal skin surface P of a user with the user's stoma S engaging (and in this drawing extending through) the stoma-receiving opening 34. FIG. 7 further illustrates the user using the fingers of his/her left hand to provide a slight finger pressure on the distal surface 24 of the carrier layer 22 of the base plate 20, while the fingers on the right hand grips a tab 40 provided on the uptake portion 38 and pulls on the tab 40 in direction of arrow A to begin removing the uptake portion 38 from the proximal surface of the removable protection element (not visible in FIG. 7). Taken-up stomal effluents 46 can be observed on the uptake portion 38 and are thereby removed, which helps ensure contamination-free application of the adhesive material of the base plate 20. It should be understood, that although identified as uptake portion 38 in FIG. 7, the component being removed by pulling on tab 40 could illustrate a simultaneous removal of the removable protection element with the uptake portion 38 provided thereon.

FIGS. 8A-8B illustrate one problem that the present invention is solving. Even a tiny little droplet of mucin on an adhesive surface can cause substantial damage. A droplet of coloured liquid 46 (illustrating mucin and coloured to enhance visibility) is placed on a glass plate illustrating the peristomal skin surface. In FIG. 8B, a second glass plate is illustrating a base plate of an ostomy appliance and is placed over the droplet 46. The droplet 46 is thereby squeezed and spread over a larger area. The contours of the squeezed droplet 46 are drawn up in FIG. 8B up to better visualize the increased size of the area now being contaminated. As can be seen, the squeezed droplet of liquid 46 now covers a much more substantial portion 47 of the glass plate. It is believed that the same mechanism applies on the surface of the adhesive material of a base plate having been subjected to stomal effluents, particularly to mucin, during application of the base plate to the peristomal skin surface around a stoma.

Figure 9B:
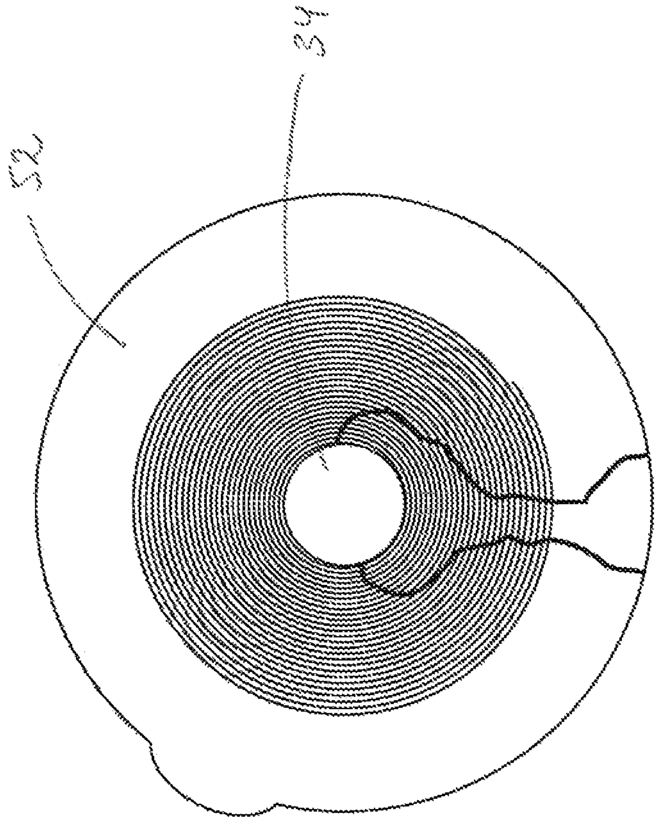
Figure 9A:
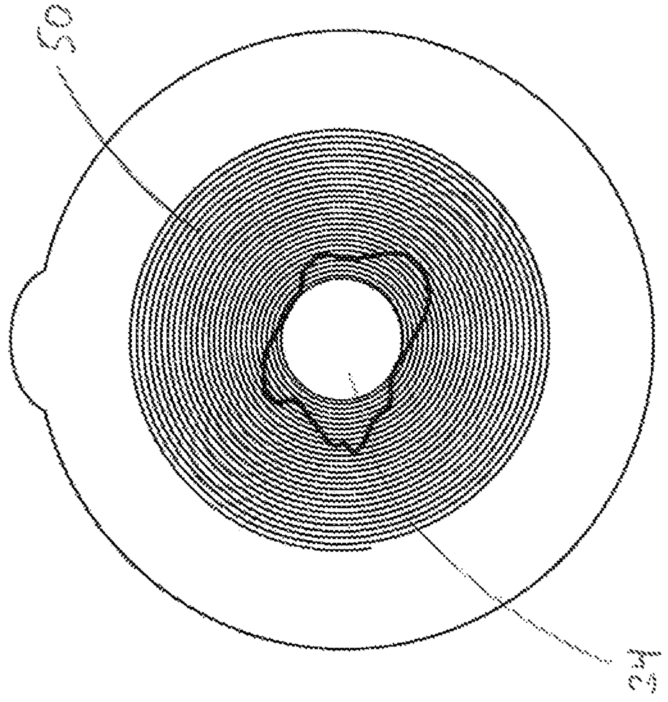

FIGS. 9A and 9B are both reproductions of photos taken during a test involving an ostomist test person to determine the extent (and partially also the speed or rate) of adhesive contamination of the adhesive material of a base plate currently available in the market. The photos of FIGS. 9A and 9B are presented to further illustrate the problem of stomal effluents, and particularly mucin, contaminating the adhesive. In the test, the base plate of a product commercially available today, in this case the Coloplast® Extended Wear™ product, was used. Two base plate product samples 50, 52 were used. For both the product sample 50 of FIG. 9A and the sample 52 of FIG. 9B, the test person customized the size and shape of the stoma-receiving opening 34 by cutting. The test person then removed the release liner from the adhesive surface of the Extended Wear™ product. For the product sample 50 of FIG. 9A, the user was asked to follow the same routine of application as in daily-life product changes, but instead of finalizing the application procedure by providing finger pressure on the distal surface of the carrier to adhere the base plate to the peristomal skin surface, the user was asked to only bring the base plate into a desired position adjacent the peristomal skin surface thereby exposing the adhesive surface to the peristomal skin surface. For sample 50 of FIG. 9A, the user was asked to then immediately remove the sample 50 from the peristomal skin surface again after having brought it into the desired position (as indicated by time t=0 written on the sample 50). For sample 52 of FIG. 9B, the user was also asked to remove the sample 52 from the peristomal skin surface again, but for sample 52 only after having waited for 2 minutes after bringing it into the desired position (as indicated by time t=2 min handwritten on sample 52). For both samples 50, 52, the influence of an otherwise unnoticeable layer of mucin on the peristomal skin surface is highlighted by marking up the portion of the adhesive surface which has become contaminated by the mucin. A dark pen was used for the marking-up of the outer limits of the extent of the contamination. Note that the contamination in this case is not caused by human waste such as faeces but is in itself unnoticeable (practically invisible to the eye) when it originates from the mucin. However, that the contamination has happened, and is very manifest when the user knows how to look for it, can be easily determined, e.g. by testing (in one simple example, just by touching with a finger) the adhesiveness/tack of the adhesive surface in the contaminated area. In the marked-up contaminated areas of the samples 50, 52 there is very little and insufficient adhesiveness/tack left in the adhesive material. It is clear that such missing adhesiveness/tack is highly problematic in that the adhesive material cannot perform in the manner it was designed to, and is consequently "off to a bad start" from the beginning of its life-time, and without this being caused by human waste (which is typically visible and therefore easier for a user to notice and handle during application of the base plate).

Figure 10:
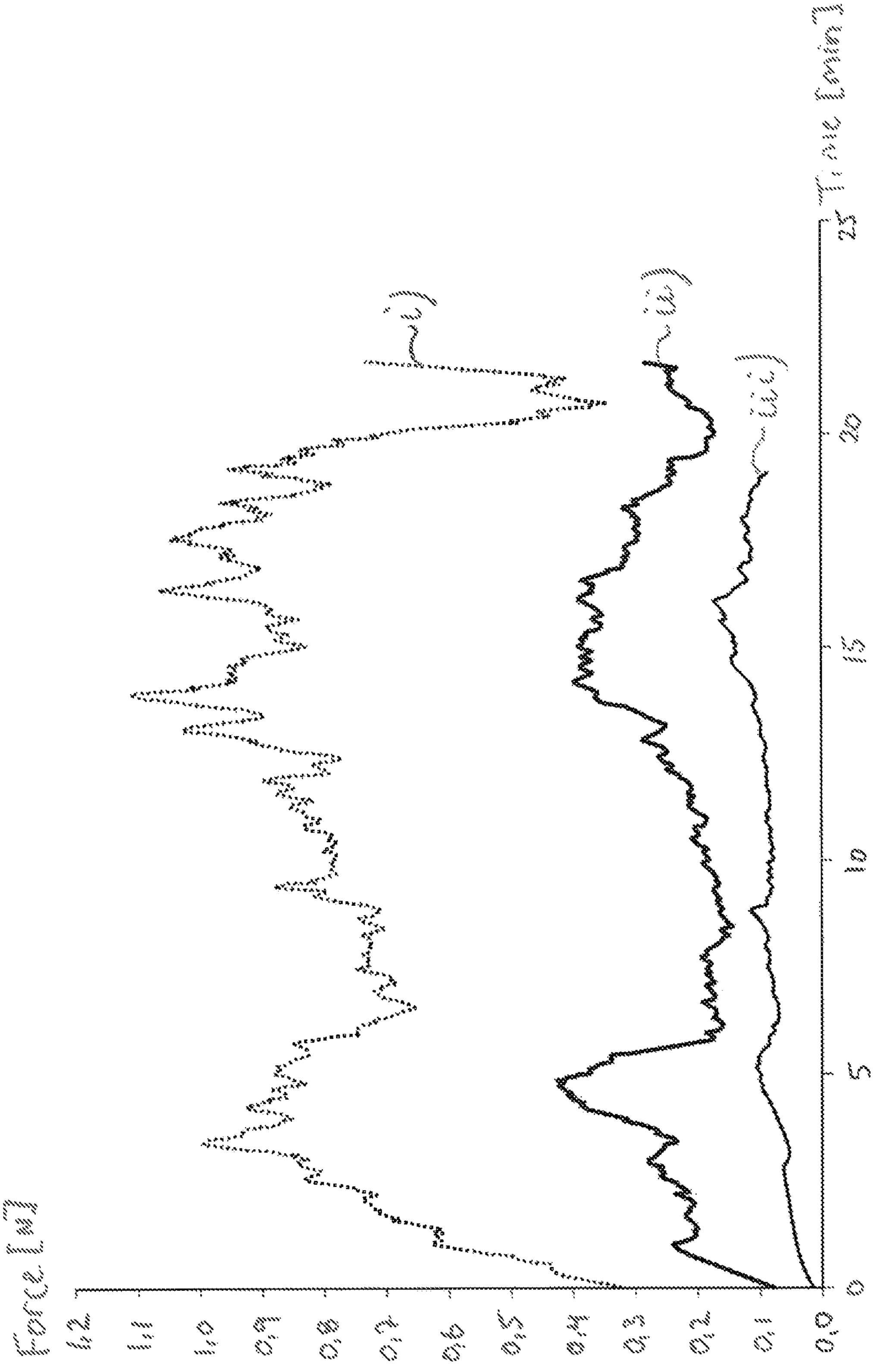
FIG. 10 is a diagram showing test results relating to the adhesiveness/tack of a pressure-sensitive adhesive of a kind widely used in the field of ostomy care, which is subjected to contamination by stomal effluents.

FIG. 10 is a diagram showing test results relating to the adhesiveness/tack of a pressure-sensitive adhesive of the PIB/SIS kind widely used in the field of ostomy care, which is subjected to contamination by stomal effluent in the form of mucin. FIG. 10 comprises three individual curves each of which illustrates a different level of mucin contamination of the surface of the adhesive material (on three individual plate samples). The diagram has time on its x-axis and force on its y-axis. The time is measured in minutes and indicates the time passed from initial mucin contamination. The force is measured in Newtons [N] and represents the adhesiveness/tack of the adhesive material of the sample as the pull force required to remove the base plate from a human skin analogue substrate. The experimental set-up is further described below.

Experimental Setup

A 90-degree peel test of the adhesives from the substrate is carried out in different modes to investigate the effect on adhesiveness/tack when the adhesive is contaminated with mucin. Equipment used includes a texture analyzer, a 500 g (0.5 kg) loadcell, and a 90-degree loadcell, at a peel speed of 0.1 mm/sec.

A human skin analogue test substrate was used (alternatively, real human skin could be used or further alternatively, animal skin, such as porcine skin, could be used).

The test adhesive material was a strip portion of the adhesive from a SenSura® Mio 1pc open ostomy appliance from Coloplast®. Three samples were prepared. The sample size was 25 mm×120 mm. The three samples were individually subjected to the following different levels of mucin contamination: sample i) No mucin contamination, the adhesive surface was completely dry and unsoiled when applied to the substrate; sample ii) moderate mucin contamination, the complete area of the adhesive surface was smeared with mucin, however, excess mucin was wiped off with tissue paper before application to the substrate; sample iii) heavy mucin contamination, the complete area of the adhesive surface was smeared with mucin and sample iii) was applied to the substrate in a practically "wet" condition.

Each of the three samples were placed on the substrate and subjected to a uniform pressure of 5 kg for 10 seconds and for each sample subjection to peeling was initiated immediately thereafter. The same substrate was used for all three individual samples. The substrate was cleaned and dried between each individual sample attachment.

Looking now at the results in the diagram of FIG. 10 and the time/force curves for each of the three individual samples i)-iii), it can be clearly observed that mucin contamination of the adhesive material causes a significant decrease in adhesiveness/tack (adhesion) and that the magnitude of mucin contamination also strongly influences the level of adhesiveness/tack. It can be observed that the curve representing sample i) (light grey colour) with no mucin contamination stabilizes at a force of about 0.9 N. The initial increase in adhesiveness/tack from about 0.3 N at time=0 min to the relatively stable value of about 0.9 N at time=~5 min is due to the adhesive material warming up to the substrate temperature and flowing better into the substrate surface until an optimum is reached. A normally desired force required to remove an adhesive base plate from the human skin ranges between 0.8 B-1.2 N. For all three sample curves, the fluctuations in the adhesiveness/tack (or force value) are caused by variations (imperfections) in the surface of the substrate encountered as the sample strip of adhesive is peeled off over the extent of the substrate.

The curve representing sample iii) (darkest colour), the heavily mucin contaminated sample, clearly shows a very limited adhesion capability, i.e. it has very little adhesiveness/tack left after being contaminated. Moreover, it can also be seen that the adhesiveness/tack does not improve, or only minimally, over the tested period. In other words, once the adhesive material of a base plate has suffered a heavy mucin contamination during application of the base plate to the peristomal skin surface, the base plate is compromised significantly from the beginning of its life-time and is consequently highly prone to the occurrence of a leakage incident. The curve representing sample ii) (grey colour), the moderately mucin contaminated sample, also shows a limited adhesion capability, however the effect of wiping off excessive mucin with tissue before application to the substrate is clearly visible. Curve ii) is believed to give a fair representation of the everyday product application situation for many users. However, for both samples ii) and iii), the detrimental effect on the adhesiveness/tack from contamination of the adhesive material during application is significant compared to the dry/clean sample i). According to the present invention, stomal effluents, including and primarily being the exuded (unnoticeable) mucin, can be removed immediately before bringing the proximal surface of the adhesive material into adhesive engagement with the peristomal skin surface. With no or only very limited effluent and/or mucin present in the adhesive interface, it is shown by the tests relating to FIG. 10 that a significantly improved adhesiveness/tack is obtained, which in turn leads to longer life-time of the individual ostomy appliances, significantly lower risk of leakage incidents, fewer skin problems for the user, lower healthcare cost-burden and in general a much better product usage compliance, all elements adding to an improved quality of life for the users.

Figure 11:
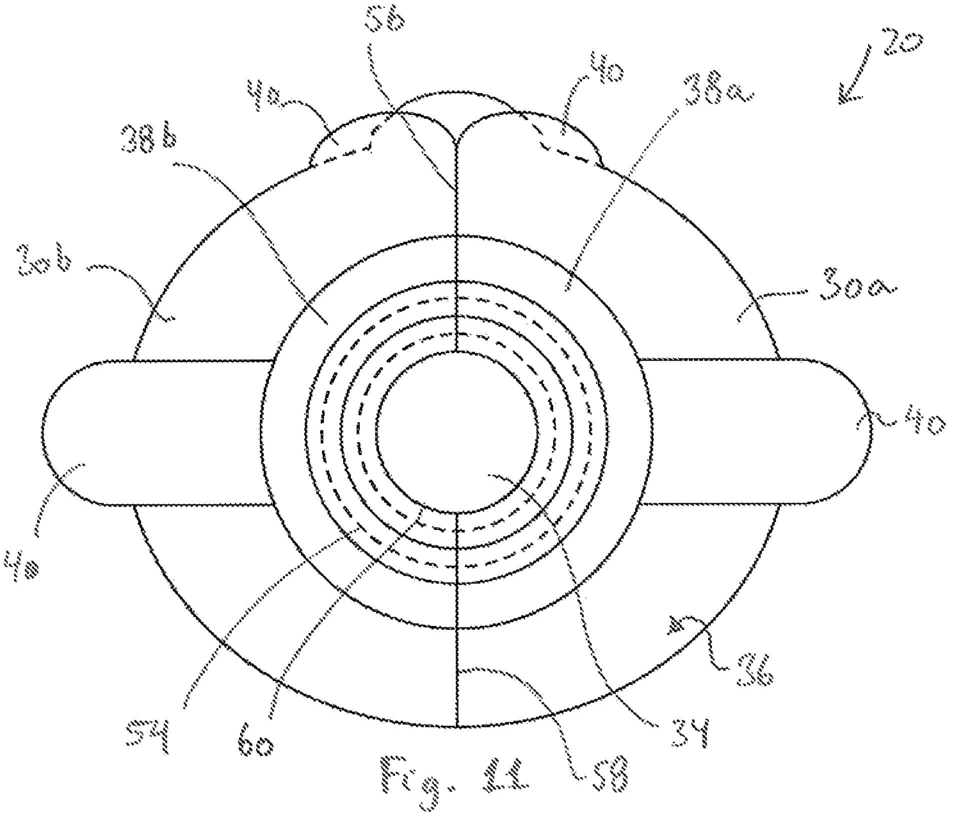

FIG. 11 is a top view of the proximally facing surfaces of one embodiment of a base plate 20 according to the disclosure. The base plate 20 includes a removable protection element 30 covering the proximal surface of an adhesive material (not visible in the figure) of the base plate. An uptake portion 38 is provided on the proximal surface 36 of the removable protection element 30. A cutting guide 54 is provided on the uptake portion 38. The cutting guide 54 includes a plurality of annular circles, e.g. printed on to a surface of the cutting guide or directly on the uptake portion 38, and provided with one set, constant distance between them (i.e. equidistant to each other). The cutting guide 54 can assist a user in customizing the stoma-receiving opening 34 to individual needs. In the embodiment, each of the uptake portion 38 and the removable protection element 30 includes two slits 56, 58 extending across the uptake portion 38 and the removable protection element 30 from a position at an inner edge 60 of the removable protection element 30 defined by the stoma-receiving opening 34 to a position on an outer peripheral edge 62 of the removable protection element 30. In this manner the two slits 56, 58 divide the uptake portion 38 into two halves 38*a*, 38*b*, and the removable protection element 30 into two halves 30*a*, 30*b*, allowing for the user to remove one half of each respective portion/element at a time. In the embodiment, the two slits 56, 58 can be considered provided along an imaginary axis extending across the base plate 20 and over the stoma-receiving opening 34. Removal facilitating means in the form of tabs 40 are provided on each half of each of the uptake portion and the removable protection element 30. The individual tabs 40 facilitate removal of the respective half portion/element one at a time to ease removal and to make the subsequent adhesive attachment more controllable.

Figure 12:
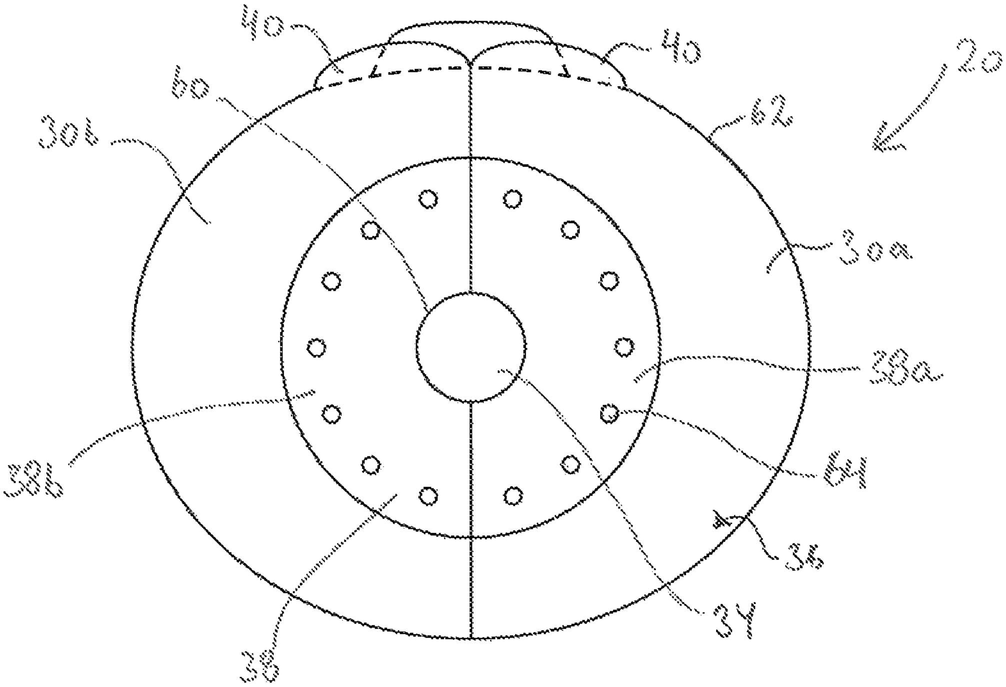

FIG. 12 is a top view of another embodiment of a base plate 20 according to the disclosure. The base plate 20 includes a removable protection element 30 covering the proximal surface of an adhesive material (not visible in the figure) of the base plate. An uptake portion 38 is provided on the proximal surface 36 of the removable protection element 30. In the embodiment, and similar to the embodiments of FIG. 11, each of the uptake portion 38 and the removable protection element 30 includes two slits 56, 58 extending across the uptake portion 38 and the removable protection element 30 from a position at an inner edge 60 of the removable protection element 30 defined by the stoma-receiving opening 34 to a position on an outer peripheral edge 62 of the removable protection element 30. Each half 38*a*, 38*b* of the uptake portion includes a plurality of indicators 64, Alternatively, the indicators 64 are provided on the proximal surface 36 of the removable protection element 30. In such embodiments, the indicators 64 can be visible in or through the uptake portion even before the indicators have been subjected to stomal effluents, however, it will be understood that the indicators will be even more visible after having been subjected to and having reacted to stomal effluents. In embodiments, the indicator is a colour indicator. A change in colour of one or more of the plurality of indicators provides the user immediately with information about the location and level of contamination of the surface. This is particularly, but not exclusively, advantageous in a training situation. One or more of the indicators 64 can have a figurative contour, such as representing a droplet or other shape. Removal facilitating means in the form of tabs 40 are provided on each half of each of the uptake portion and the removable protection element 30. The individual tabs 40 facilitate removal of the respective half portion/element one at a time to ease removal and to make the subsequent adhesive attachment more controllable.

Figure 13:
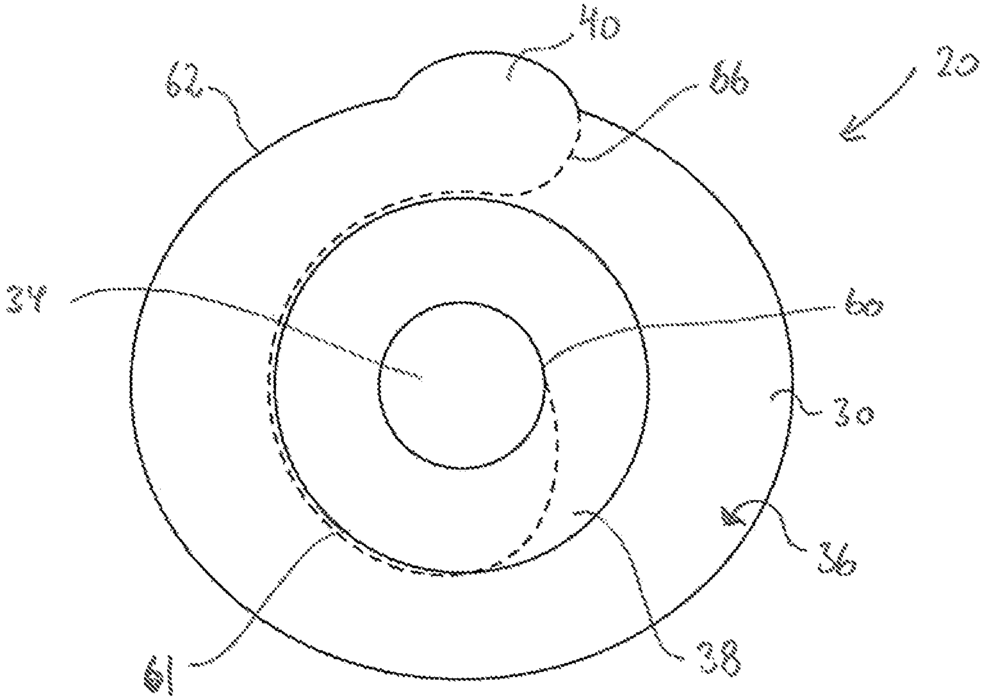

FIG. 13 is a top view of one embodiment of a base plate 20 according to the disclosure. The base plate 20 includes a removable protection element 30 covering the proximal surface of an adhesive material (not visible in the figure) of the base plate. An uptake portion 38 is provided on the proximal surface 36 of the removable protection element 30. A single slit 66 is provided in both the removable protection element 30 and in the uptake portion 38. The extent of the single slit 66 is shown in dotted line. The slit 66 generally represents a spiral figure when viewed in the top view of FIG. 13. The slit 66 extends from a position at inner peripheral edge 60 of the stoma-receiving opening 34 to a position on an outer peripheral edge 62 of the removable protection element 30 near a base of tab 40. A portion of slit 66 extends along an outer peripheral edge 61 of the uptake portion 38. In the embodiment of FIG. 13, the single slit 66 provided in the spiral shape provides a solution whereby a user can remove an entirety of both the uptake portion 38 and the removable protection element 30 in one and the same removal action.

Figure 14:
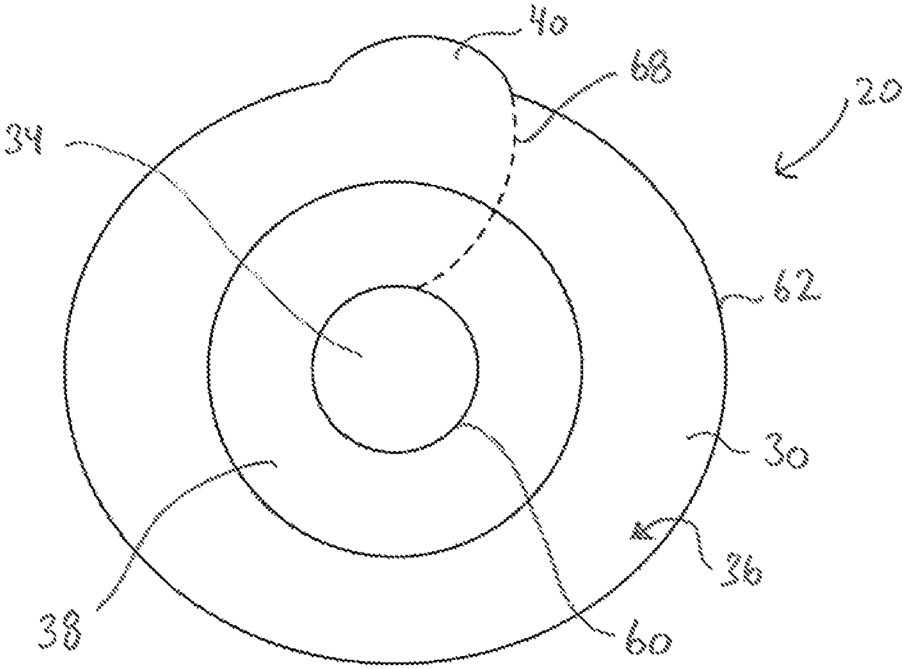

FIG. 14 is a top view of another embodiment of a base plate 20 according to the disclosure. The base plate 20 includes a removable protection element 30 covering the proximal surface of an adhesive material (not visible in the figure) of the base plate. An uptake portion 38 is provided on the proximal surface 36 of the removable protection element 30. A single slit 68 is provided in both the removable protection element 30 and in the uptake portion 38. The extent of the single slit 68 is shown in dotted line. The single slit 68 generally represents a curve or arc when viewed in the top view of FIG. 13. The single slit 68 extends from a position at inner peripheral edge 60 of the stoma-receiving opening 34 to a position on an outer peripheral edge 62 of the removable protection element 30 near a base of tab 40. The single slit 68 extends across the uptake portion 38 and removable protection element 30. In the embodiment of FIG. 14, the single slit 68 provided in the curved shape provides a solution whereby a user can remove an entirety of both the uptake portion 38 and the removable protection element 30 in one and the same removal action.

Figure 15:
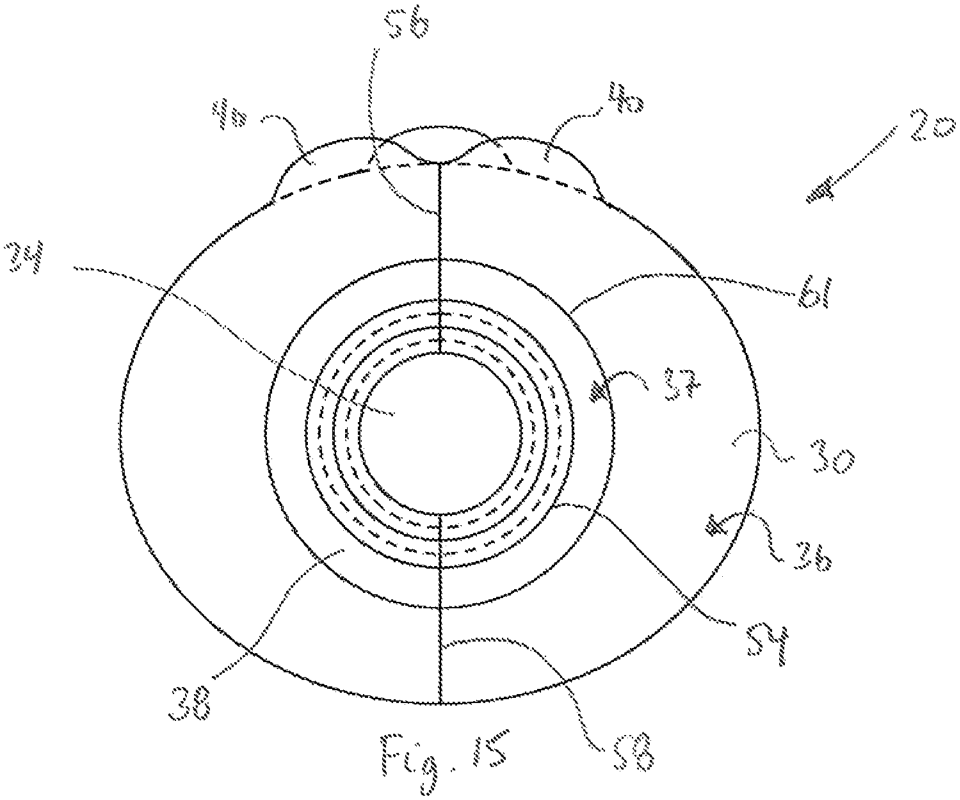

FIG. 15 is a top view of one embodiment of a base plate 20 according to the disclosure. The base plate 20 includes a removable protection element 30 covering the proximal surface of an adhesive material (not visible in the figure) of the base plate. An uptake portion 38 is provided on the proximal surface 36 of the removable protection element 30. A cutting guide 54 is provided on the uptake portion 38. The cutting guide 54 includes a plurality of annular circles, e.g. printed on to a surface of the cutting guide or directly on the uptake portion 38, and provided with one set, constant distance between them (i.e. equidistant to each other). In the embodiment of FIG. 15, the cutting guide 54 is provided as a separate label that can be adhered onto a proximal surface of the uptake portion 38 before customization of the stoma-receiving opening 30. In the embodiment, each of the uptake portion 38 and the removable protection element 30 includes two slits 56, 58 extending across the uptake portion 38 and the removable protection element 30. In this manner the two slits 56, 58 divide each of the uptake portion and the removable protection element into halves, allowing the user to remove one half at a time. Removal facilitating means in the form of tabs 40 are provided on each half the removable protection element 30. When a first of the tabs 40 is pulled, both a respective first half of the removable protection element 30 and a first half of the uptake portion 38 provided on the first half of the removable protection element 30 can be removed in a first removal action. Similarly, when a second of the tabs 40 is pulled, the respective second halves of the removable protection element 30 and the uptake portion 38 can be removed in a second removal action. This embodiment facilitates the removal of the uptake portion 38 and the removable protection element 30 and further makes the subsequent adhesive attachment more controllable.

Figure 16:
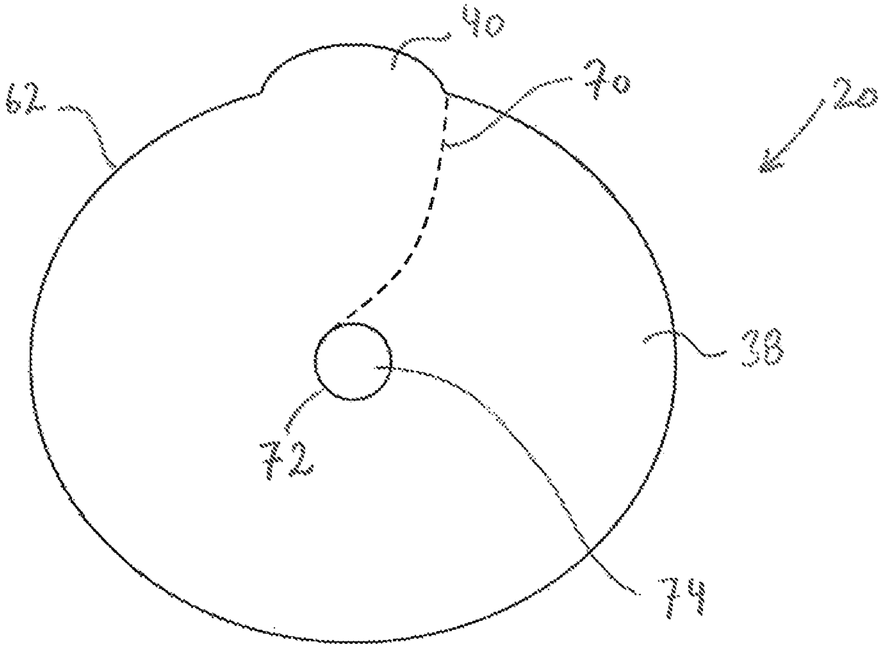

FIG. 16 is a top view of one embodiment of a base plate 20 according to the disclosure. The base plate 20 includes a removable protection element covering the proximal surface of an adhesive material. However, neither the removable protection element nor the adhesive material is visible in FIG. 16. Instead, an uptake portion 38 provided on the proximal surface of the removable protection element covers and extends over at least an entirety of the areas of the proximal surface of the removable protection element and hence also covers an area corresponding to the entire proximal surface of adhesive material. A single slit 70 is provided in the uptake portion 38. The extent of the single slit 70 is shown in dotted line. The single slit 70 generally represents a curve or arc. The single slit 70 extends from a position at inner edge of an opening 74 in the uptake portion 38 to a position on an outer peripheral edge of the uptake portion 38. The single slit 70 extends across the uptake portion 38. In the embodiment of FIG. 16, a user can remove an entirety of the uptake portion 38 and the removable protection element in one and the same removal action. In an alternative not shown, but with a top view appearance similar to FIG. 16, the uptake portion 38 is configured to form an entirety of the removable protection element and is removable in a single removal action.

In the embodiment of FIG. 16, an innermost extent of the uptake portion 38 adjacent the opening 74 forms a flexible and/or elastic flange portion 72 extending a flange distance radially inwardly beyond the inner peripheral edge (not visible) of the stoma-receiving opening of the base plate. This provides a possibility for the flange portion of the uptake portion 38 to flex in a distal direction if/when it comes into contact with a stoma surface during base plate application, which further helps prevent stomal effluents including mucin from contaminating the adhesive material of the base plate 20.

For all the embodiments of FIGS. 11-16, the uptake portion 38 can be an uptake portion 38 that is releasably adhered to the proximal surface 36 of the removable protection element 30, or the uptake portion 38 can be integral with and form at least a portion of the proximal surface 36 of the removable protection element 30.

Although specific embodiments have been illustrated and described herein, it will be appreciated by those of ordinary skill in the art that a variety of alternate and/or equivalent implementations may be substituted for the specific embodiments shown and described without departing from the scope of the present invention. The description and drawings are, accordingly, to be regarded in an illustrative rather than restrictive sense. The invention claimed is intended to cover all alternatives, modifications, and equivalents.

The invention claimed is:

1. An ostomy appliance comprising:

an ostomy base plate comprising:

a carrier layer having a distal surface and a proximal surface, an adhesive material provided on the proximal surface of the carrier layer and adapted to adhere the ostomy base plate to a peristomal skin surface around a stoma of a user, a removable protection element provided on a proximal surface of the adhesive material, a stoma-receiving opening extending through the carrier layer, the adhesive material and the removable protection element, and an uptake portion surrounding the stoma-receiving opening provided on a proximal surface of the removable protection element;

wherein the uptake portion is configured for application to the peristomal skin surface around the stoma of the user prior to adhesively affixing the ostomy base plate to the user, where the uptake portion is adapted to absorb and contain stomal effluents to prevent the adhesive material from being contaminated by the stomal effluents;

wherein at least the uptake portion, subsequent the application to the peristomal skin surface around the stoma of the user, is adapted to be removed from the ostomy base plate.

2. The ostomy appliance of claim 1, wherein the uptake portion is releasably adhered to the proximal surface of the removable protection element.

3. The ostomy appliance of claim 1, wherein the uptake portion is integral with and forms at least a portion of the proximal surface of the removable protection element.

4. The ostomy appliance of claim 1, wherein the uptake portion covers an area corresponding to less than an entirety of an area of the adhesive material provided on the proximal surface of the carrier layer.

5. The ostomy appliance of claim 1, wherein each of the uptake portion and the removable protection element comprises at least one slit extending from a position at an inner edge of the uptake portion and the removable protection element defined by the stoma-receiving opening to a position on an outer peripheral edge of each of the uptake portion and the removable protection element.

6. The ostomy appliance of claim 5, wherein the uptake portion and the removable protection element each comprises at least two slits extending from the inner edge of the uptake portion and the removable protection element and extending to the outer peripheral edge of each of the uptake portion and the removable protection element.

7. The ostomy appliance of claim 1, wherein the uptake portion comprises a circular annular wafer provided with a stoma opening.

8. The ostomy appliance of claim 1, wherein the uptake portion is provided on only a centre portion of the proximal surface of the adhesive material immediately and annularly surrounding the stoma-receiving opening, and wherein a release liner element is surrounding the uptake portion and covers a remainder of the proximal surface of the adhesive material of the base plate.

9. The ostomy appliance of claim 1, wherein the uptake portion is of greater thickness than the removable protection element.

10. The ostomy appliance of claim 1, wherein at least one of the uptake portion and the removable protection element is provided with a removal tab adapted to remove the uptake portion and the removable protection element from the base plate.

11. The ostomy appliance of claim 1, wherein the uptake portion comprises an adhesive material.

12. The ostomy appliance of claim 1, wherein the uptake portion comprises a surfactant.

13. The ostomy appliance of claim 1, wherein the uptake portion and/or the removable protection element comprise(s) a liner or sheet material.

14. The ostomy appliance of claim 1, wherein the uptake portion comprises a particulate material dusted onto the proximal surface of the removable protection element.

15. The ostomy appliance of claim 1, wherein the uptake portion comprises paper pulp.

16. The ostomy appliance of claim 1, wherein the uptake portion comprises a super-absorbent material.

17. The ostomy appliance of claim 1, wherein the removable protection element is a release liner comprising a silicone release layer provided on the proximal surface of the adhesive material of the base plate.

18. The ostomy appliance of claim 1, wherein the uptake portion has a thickness of between 50-1000 μ.

19. The ostomy appliance of claim 1, wherein the removable protection element is made from a polymeric sheet material having a thickness in a range of between 50-1000 μ, and wherein the uptake portion covers an area corresponding to less than an entirety of an area of the adhesive material provided on the proximal surface of the carrier layer, and wherein the uptake portion is of greater thickness than the removable protection element.

20. The ostomy appliance of claim 1, wherein the uptake portion is configured to have an uptake capacity ranging from 0.005 g/30 s up to 10 g/30 s of stomal effluents.

21. The ostomy appliance of claim 1, wherein the uptake portion comprises a color-change indicator adapted to change color when the stomal effluents are contained by the uptake portion.

* * * * *